us005424294A

United States Patent [19]

Della Valle et al.

[11] Patent Number: 5,424,294
[45] Date of Patent: Jun. 13, 1995

[54] MODIFIED GANGLIOSIDES AND THE FUNCTIONAL DERIVATIVES THEREOF

[75] Inventors: Francesco Della Valle, Padua; Aurelio Romeo, Rome, both of Italy

[73] Assignee: Fidia S.p.A., Abano Terme, Italy

[21] Appl. No.: 138,184

[22] Filed: Oct. 20, 1993

Related U.S. Application Data

[62] Division of Ser. No. 611,700, Nov. 13, 1990, Pat. No. 5,264,424.

Foreign Application Priority Data

Nov. 14, 1989 [IT] Italy ................................ 48554/89

[51] Int. Cl.$^6$ .............................................. A61K 31/70
[52] U.S. Cl. ........................................ 514/25; 514/53; 514/54; 514/61; 536/4.1; 536/53; 536/55.1; 536/55.3; 536/123
[58] Field of Search ................. 514/25, 53, 54, 61; 536/4.1, 53, 55.1, 55.3, 123

[56] References Cited

U.S. PATENT DOCUMENTS

| | | | |
|---|---|---|---|
| 4,476,119 | 10/1984 | Della Valle et al. | 536/53 |
| 4,593,091 | 6/1986 | Della Valle et al. | 536/53 |
| 4,713,374 | 12/1987 | Della Valle et al. | 536/54 |
| 4,716,223 | 12/1987 | Della Valle et al. | 536/53 |

FOREIGN PATENT DOCUMENTS

| | | |
|---|---|---|
| 0072286 | 2/1983 | European Pat. Off. . |
| 0195169 | 9/1986 | European Pat. Off. . |
| 0373039 | 6/1990 | European Pat. Off. . |
| 2549680 | 2/1977 | Germany . |

OTHER PUBLICATIONS

S. Neuenhofer et al, Biochem. vol. 24 (1985) pp. 525–532.
R. Kannagi et al, Proc. Natl. Acad. Sci. USA, vol. 79 (1982) Biochem. pp. 3470–3474.
W. Sonnino et al, Chemistry and Physics of Lipids, vol. 42 (1986) pp. 3–26.
S. Sonnino et al, Journal of Lipid Research, vol. 26, No. 2 (1985) pp. 248–257.
W. Song et al, Biochemistry, vol. 28 (1989) pp. 4194–4200 Chemical Abstract vol. 110, Formula Index 4100F 1989.
Y. Hirabayashi et al, J. Biochem. vol. 103, No. 1 (1988) pp. 1–4.
P. H. Fishman et al, Journal of Biological Chemistry, vol. 255, No. 16 (1980) pp. 7657–7664.
Biol. Chem. Hoppe Seyler, vol. 367, suppl (1986) p. 241.
G. A. Nores et al, Carbohydrate Research, vol. 179 (1988) pp. 393–410.
N. Hanai et al, Biochemical and Biophysical Research Communications, vol. 147, No. 1 (1987) pp. 127–134.
T. Mosmann, Journal of Immunological Methods, vol. 65 (1983) pp. 55–63.
Engelsen *Acta Neurol. Scand.* 1986, 74, 337–355.
Olney *Ann. Rev. Pharmacol. Toxicol.* 1990, 20, 47–71.
Miceli et al. *Acta Psychiat. Scand.* 1977, 55, 102.
Grillo *Eur. Medicophys.* 1977, 13, 1.
Ceccarelli et al. *Adv. Exp. Med. Biol.* 1976, 71, 275.
Gorio et al. *Brain Res.* 1980, 197, 236.
Leon et al. *J. Neurochem.* 1981, 37, 350.
Brunngraber et al. "Extraction and Analysis of Materials Containing Lipid Bound Sialic Acid" 1976, 159–186.
Ledeen et al. "Gangliosides of the Nervous System", 187–214.
Klein et al. *Eur. J. Biochem.* 1987, 167, 417–424.
Sonnino et al. *Biochemistry* 1989, 28, 77–84.
Kogtev et al. CA110:147995b, 1989 (M. M. Shemyakin Inst. Bioorg. Chem., Moscow USSR).
Sugimoto et al. CA112:56S73n, 1990 (Shionogi & Co. Ltd.).
Electromyogr. Clin. Neurophysiol. 19, 353, (1979).
Minerva Medica, 69, 3277 (1978).
Minerva Stomat. 27, 177, (1978).
Med. Del Larvoro, 68, 296 (1977).

*Primary Examiner*—Douglas W. Robinson
*Assistant Examiner*—Kathleen Kahler Fonda

[57] ABSTRACT

N-acyl-N,N'-di-lysogangliosides, N'-acyl-N,N'-di-lysogangliosides and N,N'-diacyl-N,N'-di-lysogangliosides, in which the acyl groups are derived from an organic acid of the aliphatic, aromatic, araliphatic, alicyclic or heterocyclic series and in which at least one of the two acyl groups is not aliphatic, and their preparation are disclosed. Also disclosed is the preparation of the esters, inner esters, amides and hydroxy peracylates of these compounds and salts thereof. These compounds are useful in the treatment of pathologies of the central and peripheral nervous systems.

2 Claims, No Drawings

MODIFIED GANGLIOSIDES AND THE FUNCTIONAL DERIVATIVES THEREOF

This application is a divisional of application Ser. No. 07/611,700 filed on Nov. 13, 1990, U.S. Pat. No. 5,264,424, the entire contents of which are hereby incorporated by reference.

SUMMARY

The present invention concerns modified gangliosides and their functional derivatives, and more precisely N-acyl-N,N'-di-lysogangliosides, N'-acyl-N,N'-di-lysogangliosides and N,N'-diacyl-N,N'-di-lysogangliosides, in which the acyl groups are derived from an organic acid of the aliphatic, aromatic, araliphatic, alicyclic or heterocyclic series and in which at least one of the two acyl groups is not aliphatic, their esters, inner esters, amides and hydroxy peracylates and their salts.

The invention is also directed to pharmaceutical preparations containing one or more of the aforesaid ganglioside derivatives or their salts, as well as the therapeutic use thereof and methods for their preparation.

The basic ganglioside of the novel derivatives of the invention can be any one of those extracted from natural products and in particular from the central and peripheral nervous systems of vertebrates, but also those from the adrenal medulla, from erythrocytes, from the spleen or from other organs. They are preferably purified gangliosides, which, although not unitary chemical compounds, are identifiable by an approximate formula including an oligosaccharide part, generally chemically well-defined for each ganglioside, a sialic part (that is, constituted by one or more sialic acids) and a ceramide part, the last two parts generally constituted by a mixture of various sialic acids and various N-acyl-sphingosines varying in the lengths of their aliphatic chains and with various acyls derived from higher fatty acids. The approximate formula of such a ganglioside can be represented as follows

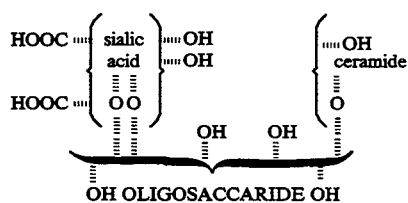

(I)

where the sialic acids have the general formula

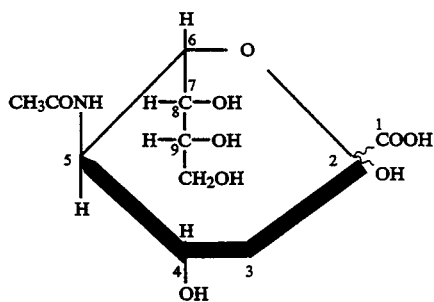

(II)

in which one or more of the primary or secondary hydroxy groups can also be acylated and in which the acyl groups are derived from acetic or glycolic acid and the "ceramide" residue corresponds to one of the formulae:

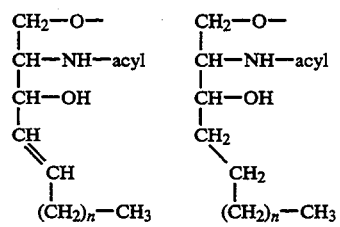

in which n is 6–18 and the acyl group is derived from a saturated or unsaturated fatty acid having from 16 to 22 carbon atoms or from a corresponding hydroxy acid. The novel derivatives of the invention differ with respect to the nature of this acyl. The acyl moiety is unitary therein, while in gangliosides it is a mixture derived from various aliphatic acids having from 16 to 22 carbon atoms. Another difference is that the acyl belongs to a series of carboxy acids which are not naturally occurring, as opposed to gangliosides, that is, to acids of the aromatic, alicyclic or heterocyclic series. They are therefore semisynthetic ganglioside derivatives containing an unnatural ceramide.

The number of sialic acids present in gangliosides usually varies from 1 to 5. The sialic residues are bound to the oligosaccharide by a ketose-type bond formed by the hydroxyl in the 2-position with a hydroxyl of the oligosaccharide.

When several sialic acids are bound together, the union of their molecules is brought about by ketose bonds formed between the hydroxyl groups at the 2-and 8-position of two sialic acid molecules. The sialic acids of gangliosides, including those which are purified as described previously, are mixtures of various chemically unitary acids, for example N-acetylneuraminic acid and N-glycolylneuraminic acid, predominantly the former, and possibly of one or more of their O-acyl derivatives, for example, 8-O-acyl derivatives.

The oligosaccharide is composed of a maximum of 5 monosaccharides or their derivatives with an acylamino group, especially hexoses and their derivatives of the aforesaid type. At least one glucose or galactose molecule is however present in the oligosaccharide. The most frequent residue as an acylamino derivative of the aforesaid sugars is N-acetylgucosamine and N-acetylgalactosamine.

To better illustrate the structure of the gangliosides included in formula (I), which is essentially that of the derivatives of the invention, and in particular the character of the bonds between the saccharide part, the sialic acids and the ceramide, presented herewith in its entirety is the formula of a "pure" ganglioside $GM_1$ containing one single sialic acid (represented by N-acetylneuraminic or N-glycolylneuraminic acid):

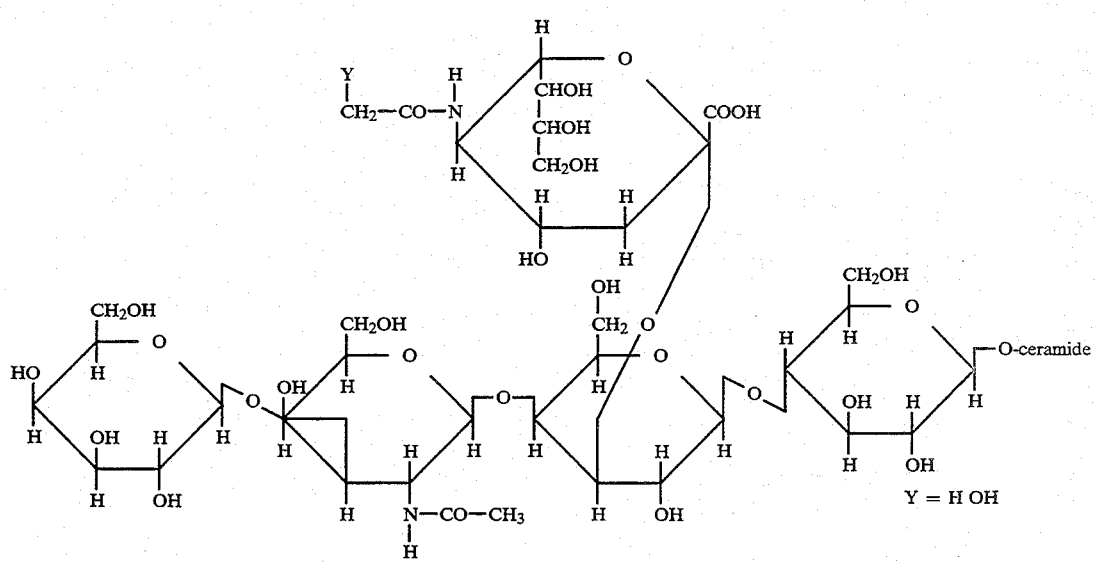

The formula is essentially the same for derivatives of the ganglioside "GM₁" according to the present invention with the ceramide residue substituted by a corresponding "artificial" ceramide, the N-acyl group of which is derived from one of the acids of the aromatic, alicyclic or heterocyclic series.

The term "lysoganglioside" is used in the literature to designate compounds derived from natural gangliosides by elimination of the acyl group present on the sphingosine nitrogen therein. It can be eliminated enzymatically, for example, by exposing the gangliosides to the action of the glycosphingolipid-ceramide-deacylase enzyme. This type of hydrolysis leaves intact the acylamino and acylhydroxy groups in the residues of neuraminic acid. To deacylate these groups also, thus obtaining a ganglioside derivative containing two free amino groups, both on the sphingosine nitrogen and on the neuraminic nitrogen, chemical hydrolysis must be used, for example, with dilute potassium hydroxide. The ganglioside derivatives obtained by deacylation on the neuraminic nitrogen in the manner described herein are usually known in the literature by the term "de-N-acetyl-gangliosides", the acyl group in this position being the acetyl group. Designating the two nitrogen atoms of the sphingosine residue and in the neuraminic residue as N and N' respectively, the term "N'-lysoganglioside" can also be used for the aforesaid de-N-acetyl-gangliosides, and similarly, the term "lysogangliosides" can be used for derivatives with the free amino group in the sphingosine residue, which should therefore be more precisely identified by the term "N-lysogangliosides". The term "N,N'-di-lysogangliosides" refers, on the other hand, to the compound with both free amino groups. This nomenclature will be used throughout the present application.

The aforesaid definition of the derivatives according to the invention includes the group of ganglioside derivatives which present an acetyl group on the neuraminic nitrogen and an aromatic, araliphatic, alicyclic or heterocyclic acyl on the sphingosine nitrogen.

The invention also includes N-acyl-lysogangliosides of this kind derived from the aforesaid lysogangliosides obtained enzymatically and which therefore contain in their sialic acids the acyl groups present in natural gangliosides, and mixtures of acylamino groups derived mostly from acetic acid and to a lesser extent glycolic acid, and possibly acyl groups which esterify the hydroxy groups. The term "N-lysogangliosides" or "N-acyl-lysogangliosides" will therefore be used in the following description of the invention both for these derivatives, which will be qualified as "natural" (for example, natural N-lyso GM₁), and for those which possess a unitary acetyl group on the neuraminic nitrogen, which will be designated without this description or preferably as derivatives of N,N'-di-lysogangliosides, for example, N-benzoyl-N'-acetyl-N,N'-di-lyso GM₃.

The term "acyl-dilysogangliosides" will hereafter be used to signify all the new compounds of the invention. As will be detailed hereafter, it is possible to selectively deacylate a ganglioside on the neuraminic nitrogen and on the hydroxy groups alone, for example with a dilute alkaline hydroxide. By acylating the amino group of the neuraminic residue in these compounds with a different acyl from the acetyl (and glycolyl), N,N'-diacyl-N,N'-di-lysogangliosides are obtained which also conserve a natural part of gangliosides, that is, the mixed acyl group derived from higher aliphatic acids on the sphingosine nitrogen. These derivatives, which constitute a preferred group of the new compounds according to the present invention, will be designated as N'-acyl-N'-lysogangliosides, for example, N'-benzoyl-N'-lyso GM₁. It is well known that gangliosides play an important role in the nervous system and it has recently been demonstrated that they are useful in therapy for pathologies of the peripheral nervous system and in pathologies of the central nervous system [Acta Psychiat. Scand., 55, 102, (1977); Eur. Medicophys.,13, 1, (1977); Ric. Sci. Educ. Perm. Suppl. 9, 115, (1978); Adv. Exp. Med. Biol. 71, 275, (1976); Electromyogr. Clin. Neurophysiol., 19, 353, (1979); Minerva Medica, 69, 3277, (1978); Minerva Stomat., 27, 177, (1978); Med. del Lavoro, 68, 296 (1977); Brain Res. 197, 236, (1980)]. The therapeutic action of gangliosides seems to consist mainly in stimulation of sprouting phenomena in nerve cells and in activating the enzymes involved in the conduction of nervous stimuli, such as the $(Na^+,K^+)$ ATPase enzyme [Brain Res., 197, 236 (1980), J. of Neurochem. 37, 350 (1981)]. Neuronal sprouting stimulated by gangliosides enhances the functional recovery of impaired or damaged nerve tissue.

Further studies have been carried out to find compounds which may prove more efficient than gangliosides in therapies for nervous system pathologies. These studies have led for example to the discovery that ganglioside inner esters, in which one or more hydroxyls of the saccharide part are esterified with one or more carboxy groups of the sialic acids (intramolecular reaction) with the formation of the same number of lactone rings, are more active than gangliosides themselves in enhancing neuronal sprouting and in activating the membrane enzymes involved in the conduction of nerve stimuli, such as the enzyme $(Na^+,K^+)$ATPase (see for example U.S. Pat. Nos. 4,476,119, 4,593,091 and 4,716,223).

"Outer" esters of gangliosides, that is, esters of the carboxy functions of the sialic acids with various alcohols of the aliphatic, araliphatic, alicyclic or heterocyclic series, also show an improved activity on neuronal sprouting and conduction of nervous stimuli. The amides of gangliosides also possess the same properties, as do the peracylated derivatives of amides, esters and simple gangliosides. All of these derivatives, which are described in U.S. Pat. No. 4,713,374, are also to be considered as basic substances for the acyl-di-lysogangliosides of the present invention.

The new compounds of the present invention are semisynthetic ganglioside analogues and differ from the prior art molecules due to the presence of N-acyl groups, both on the sphingosine nitrogen, and on the neuraminic nitrogen. They are not "natural", and therefore have at least one acyl group derived from acids of the aromatic, araliphatic, alicyclic or heterocyclic series. Furthermore, they differ from natural gangliosides (with the aforesaid exception of "natural" N-acyl-N-lysogangliosides and N'-acyl-N'-lysogangliosides) because of the fact that the acyl groups are unitary and well-defined. Those derivatives which contain a different acyl group from acetyl on the neuraminic nitrogen, can be acyl groups of the type present in natural gangliosides, that is, mixtures of higher fatty acids, such as stearic or palmitic acid.

At the basis of the present invention is the discovery that the new "semisynthetic" gangliosides also possess essentially the same pharmacological actions as natural gangliosides and their esters, amides, inner esters and peracylated derivatives of all of these compounds, with a range of action that is modified with respect to many parameters, such as the rate of "onset", duration and intensity of the sprouting action of neuronal cells, and which can be regulated according to the greater or lesser lipophilic or hydrophilic character of the acyl component, or the type and extent of side effects, which in some cases can prove to be negative or positive, according to the therapeutic problem being tackled. An example is the inhibiting action on protein kinase C, which can be an undesirable and negative effect in certain conditions of imbalance of the normal mechanisms of neurotransmission functions. Activation is triggered by an increased concentration of excitatory amino acids such as glutamic and/or aspartic acid. These acids have, under the aforesaid abnormal conditions, a direct toxic action on neuronal cells. One great advantage of the products of the present invention, which sets them apart from other protein kinase C inhibitors, such as gangliosides themselves or sphingosine, consists in their ability to prevent and combat the aforesaid neurotoxic action.

It is important to emphasize that the products of the present invention, unlike calcium antagonists and glutamate receptor antagonists (NMDA in particular), act only in the presence of abnormal conditions, and therefore limit localized neurotoxicity and maintain neuronal plasticity, thereby allowing a more ready recovery of the impaired physiological functions. In many cases it is possible to use the derivatives of the invention to make use of the action of the acids themselves, corresponding to a given acyl group, avoiding the specific action of the ganglioside part, which in such cases functions as a vehicle. This is the case, for example, with the new type of ganglioside ill which the N-acyl group is derived from an acid which is active on the central or peripheral nervous system, such as lysergic acid and its analogues, or nicotinic and isonicotinic acids. These acids have a certain action in vitro, but hardly any or no action at all in vivo. When they are introduced into the molecule of a ganglioside according to the present invention, the action appears to its full extent in vivo.

The ganglioside derivatives of the present invention can therefore be used instead of natural products or the aforesaid already known semi-synthetic derivatives. They are of great value in cases of patients who do not respond satisfactorily to conventional products or in cases which present individual idiosyncrasies or allergies. Moreover, they can be used as vehicles because of the specific pharmacological action of the acid corresponding to the N-acyl group.

The lysogangliosides which serve as the base for the preparation of the new acyl-di-lysogangliosides according to the present invention are above all those obtainable by deacylation of gangliosides found in natural products, and in particular in tissues of the central and peripheral nervous systems of vertebrates, and also in adrenal medulla, erythrocytes, the spleen or in other organs. They can be purified gangliosides, such as those which are defined by this term in the literature and are represented by a unitary structure with regard to the saccharide part, or they can be mixtures of gangliosides. Among the most important gangliosides to be used as starting bases for the derivatives of the invention can be mentioned, for example, those in which the oligosaccharide is formed by a maximum of 4 hexose residues, and in which this saccharide part is chemically unitary. The hexoses are preferably chosen from the group formed by N-acetylglucosamine and N-acetylgalactosamine (ganglioside group A). The gangliosides of this group are, for example, those extracted from the brains of vertebrates, such as those described in the article "Gangliosides of the Nervous System" in "Glycolipid Methodology", Lloyd A., Witting Ed., American Oil Chemists Society, Champaign, Ill. 187-214 (1976) (see especially Table 1), for example the gangliosides $G_{M4}$, $G_{M3}$, $G_{M2}$, $G_{M1}$-GlcNAC, $G_{D2}$, $G_{D1a}$-GalNAC, $G_{T1c}$, $G_Q$, and $G_{T1}$ and, in particular, those in which the oligosaccharide contains at least one glucose residue or galactose residue and either N-acetylglucosamine or N-acetylgalactosamine and preferably the following (ganglioside group B):

$G_{M1}$

Gal(1→3)GalNAC(1→4)Gal(1→4)Glc(1→1) Ceramide

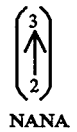

NANA $G_{D1a}$

$G_{D1b}$

Gal(1→3)GalNAC(1→4)Gal(1→4)Glc(1→1) Ceramide

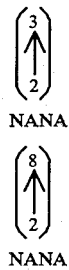

$G_{T1b}$

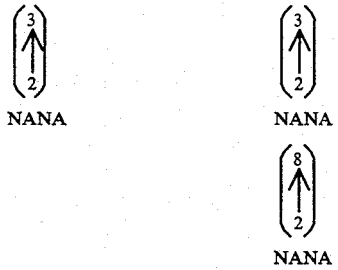

where Glc stands for glucose, GalNAC stands for N-acetylgalactosamine, Gal stands for galactose, and NANA stands for N-acetylneuraminic acid.

The present invention also includes mixtures of the new N-acyl-lysogangliosides and in particular those which are derived from the ganglioside mixtures present in extracts from various animal tissues, such as in "total" extracts, or in various fractions, for example those described in the literature. Examples of such literature include the articles mentioned previously or the articles "Extraction and analysis of materials containing lipid bound sialic acid" in the aforesaid journal, pages 159–186 (1976) and in "Gangliosides of the Nervous System" same publication, pages 187–214, and in the German patent No. 2549680. In these new mixtures the N-acyl part of the ganglioside mixtures is substituted by one of the aforesaid acyl groups, and they can be obtained according to the procedure of the present invention as disclosed hereafter by deacylation of the ganglioside mixtures and subsequent reacylation, optionally after the reacylation of other deacylated groups in the sialic part of the gangliosides. Among the most important ganglioside mixtures to be used as starting products are ganglioside extracts obtained from the nervous system, in particular from the brain and containing the gangliosides $GM_1$, $G_{D1a}$, $G_{D1b}$ and $G_{T1b}$, already mentioned.

As noted above, at the basis of the present invention is the discovery that the new semisynthetic ganglioside analogues described herein and their aforesaid functional derivatives or their salts possess essentially the same pharmacological actions as natural gangliosides or their analogous functional derivatives, with a range of action which differs with regard to many parameters.

These modified gangliosides also possess an inhibiting action on protein kinase C activation.

The aforesaid pharmacological properties of the modified gangliosides of the invention can be illustrated by the following experiments.

In primary neuronal cell cultures, stimulation of excitatory amino acid (EAA) receptors enhances the increase in $Ca^{+2}$ influx and translocation, with the consequent activation of protein kinase C (PKC) from the cytosol to the membranes. The addition of glutamate or exposure to anoxic conditions of primary cultures of granular cells induces cell damage leading to neuronal death. Acute cerebral ischemia is followed by an alteration in glutamergic transmission which triggers a cascade of events leading, as occurs in vitro, to cell death.

It is known that pre-exposure of primary neuronal cultures to trisialosyl-N-tetraglycosylceramide ($GT_{1b}$) or monosialosyl-N-tetraglycosylceramide ($GM_1$) inhibits PKC translocation and protects against glutamate-induced cell death.

Binding tests have shown that the action mechanism of gangliosides is not linked with receptor antagonism.

Reported here are the experiments conducted with the ganglioside derivatives N'-3,4,5-trimethoxybenzoyl-N'-lyso $GM_1$ (Ligade 5), N-(2-furoyl)-N-lyso $GM_1$ (Ligade 34), N-(1-methyl-2-pyrrol-carbonyl)-N-lyso $GM_1$ (Ligade 38), N-(2-thiopheneacetyl)-N-lyso $GM_1$ (Ligade 45), N,N'-di-phenylacetyl-di-lyso $GM_1$ (Ligade 82), N,N'-di-(2-pyridylacetyl)-di-lyso $GM_1$ (Ligade 84), and N,N'-di-(5-methyl-2-thiophenecarboxyl)-di-lyso $GM_1$ (Ligade 85), which are suitable for the assessment of the capacity to antagonize selective neuronal death induced by glutamate.

MATERIALS AND METHODS

Cell cultures

Primary cultures of cerebellar granule cells from 8-day-old Sprague Dawley rats, composed of >90% of granule cells, approximately 5% of GABAergic neurons and <5% of glial cells, were employed. In these experiments, cells were used on the 12th day of culture.

Induction of neurotoxicity with glutamate

The glutamate (100 μm in Locke's solution without $Mg^{+2}$) was added to the cells and left to stand for 15 minutes at room temperature (controls had no glutamate); the cultures were washed 3 times with Locke's solution to remove the excess glutamate, then replated in the original culture medium.

Solubilization, incubation of the compound and method of analysis

Ligade 5, 34, 38, 45, 82, 84 and 85 were dissolved in chloroform/methanol 2:1, dried in $N_2$, resuspended in Locke's solution plus $Mg^{+2}$ at a final concentration of $5\times10^{-6}M$ and added to the cultures at 37° C. 15 minutes before induction of neurotoxicity. The $GM_1$, similarly solubilized, and used at a final concentration of $1\times10^{-4}M$, was added to the cells 120 minutes before exposure to L-GLU.

Cell survival was assessed 24 hrs later by the colorimetric method (D.O. 570–630) using MTT (3-4,5-dimethylthiazole-2-yl)-2,5-diphenyl-tetrazolium).

RESULTS

The experiments showed that Ligade 5, 34, 38, 45, 82, 84 and 85, at a concentration of $5\times10^{-6}M$ and $GM_1$ at a concentration of $1\times10^{-4}M$ used as control, proved effective in protecting against glutamate-induced neurotoxicity ($p<0.05$) (Table 1).

It should be noted that the Ligade derivatives are efficacious at doses 10 times less than those required by $GM_1$ and after far shorter preincubation times.

DISCUSSION

The results obtained clearly indicate that the new ganglioside derivatives, named Ligade 5, 34, 38, 45, 82, 84 and 85, are able to antagonize glutamate-induced neurotoxicity in primary cultures of cerebellar granule cells.

The effect of the new derivatives is particularly interesting since it is observed at concentrations over 10 times less than those of $GM_1$ at corresponding levels of efficacy, and after shorter periods of preincubation.

With regard to this effect, the derivatives of the invention can be recommended in acute and chronic pathologies based on glutamergic-type damage, such as cerebral ischemia, trauma, epilepsy, chorea, Parkinson's disease, aging and dementia as well as brain disorders, hypoglycemia and hypoxia. Some of the mechanisms at the basis of brain damage, especially with regard to neurotoxicity, are however common to damage to other systems too, such as the neurocardiovascular system.

TABLE 1

Protective effect of Ligade 5, 34, 38, 45, 82, 84 and 85 and $GM_1$ in a model of neurotoxicity induced by exogenous glutamate in primary cultures of cerebellar granule cells.

| compound | cell survival MTT (DO 570-630) |
| --- | --- |
| control Locke's solution-$Mg^{+2}$ | $0.156 \pm 0.021$ |
| L-Glutamate | $0.103 \pm 0.004$ |
| L-Glu + Ligade 5 | $0.147 \pm 0.014$ |
| L-Glu + Ligade 34 | $0.126 \pm 0.003$ |
| L-Glu + Ligade 38 | $0.131 \pm 0.003$ |
| L-Glu + Ligade 45 | $0.138 \pm 0.006$ |
| L-Glu + Ligade 82 | $0.165 \pm 0.006$ |
| L-Glu + Ligade 84 | $0.151 \pm 0.007$ |
| L-Glu + Ligade 85 | $0.126 \pm 0.008$ |
| L-Glu + $GM^1$ | $0.133 \pm 0.018$ |

The granule cells were used on the 12th day of culture and were exposed, at room temperature, to 100 μM L-glutamate (L-GLU) for 15 minutes. The Ligade derivatives, solubilized in Locke's solution at a final concentration of $5\times10^{-6}M$, were added to the cells 15 minutes before induction of neurotoxicity, while the $GM_1$ $1\times10^{-4}M$ was pre-incubated for 120 minutes. $p<0.05$ for $GM_1$ and Ligade derivatives vs. L-GLU.

In view of the pharmacological properties described above, the aforesaid semisynthetic ganglioside analogues can be used as drugs in the following pathologies: cerebral ischemia, metabolic encephalopathies such as hypoglycemia and hypoxia, encephalopathies of toxic origin, trauma, epilepsy, neurodegenerative diseases such as Parkinson's disease and Huntington's chorea, and mental disorders.

Administration is usually by injection, intramuscular, subcutaneous, intravenous, transdermal or pulmonary administration, preferably in suitably buffered aqueous solutions. Safe storage of the pharmaceutical can be ensured by preparing it in the form of vials containing solutions of the derivative, optionally together with other auxiliary ingredients, as will shown hereafter in the case of the pharmaceutical preparations of the present invention. For the therapeutic, or possibly also preventive, application by the aforesaid parenteral route, the dosage varies preferably from 0.05 mg to 5 mg of active substance per kg of body weight/day and especially between 0.05 mg and 2 mg per kg of body weight/day.

Although the new therapeutic applications according to the invention are generally suitable for use in all pathologies connected with nerve conduction impairments in the central and peripheral nervous systems, the following can be specifically mentioned: retrobulbar optical neuritis, paralysis of the oculomotor nerves, trigeminal neuralgia, paralysis of the facial nerve and Bell's palsy, Garcin's syndrome, traumatic lesions of the peripheral nerves, diabetic and alcoholic polyneuritis, obstetrical paralysis, paralytic sciatica, motor neuron disease, amyotrophic lateral sclerosis, myelopathic muscular atrophy, progressive bulbar paralysis, myasthenia gravis and Lambert Eaton's syndrome, muscular dystrophy, impairments in synaptic nerve transmission in the CNS and PNS, and consciousness deficiencies such as confusion, concussion, thrombosis and embolism.

The invention also includes the functional derivatives of the sialic carboxy groups of the new acyl-lysogangliosides, that is, esters and amides, and also inner esters with lactone bonds between the sialic carboxy groups and the hydroxyls of the oligosaccharide, similar to those of gangliosides as well as the derivatives peracylated on the ganglioside hydroxyls, both of acyl-lysogangliosides, and of their aforesaid functional derivatives, and the salts of all the new acyl-di-lyso-gangliosides and of their functional derivatives. These sialic functional derivatives can be obtained from the new acyl-di-lysogangliosides by the procedures described in the various aforesaid patents for the corresponding ganglioside derivatives.

The invention includes in particular also mixtures of these derivatives, such as are obtained from mixtures of acyl-lysogangliosides according to the invention, obtained in turn from the aforesaid ganglioside mixtures.

The ester groups of the new N-acyl lysoganglioside derivatives of the invention are derived particularly from alcohols of the aliphatic series and especially from those with a maximum of 12 and especially 6 carbon atoms, or of the araliphatic series with preferably only one benzene ring, optionally substituted by 1–3 lower alkyl groups ($C_{1-4}$), for example methyl groups, and a maximum of 4 carbon atoms in the aliphatic chain, or by alcohols of the alicyclic or aliphatic alicyclic series with only one cycloaliphatic ring and a maximum of 14 carbon atoms, or of the heterocyclic series with a maximum of 12 and especially 6 carbon atoms and only one heterocyclic ring containing a heteroatom chosen from the group formed by N, O and S. The amide groups of the carboxy functions in the N-acyl lysoganglioside derivatives of the present invention are derived from ammonia or from amines of any class, with preferably a maximum of 12 carbon atoms.

The aforesaid alcohols and amines can be unsubstituted or substituted, especially by functions chosen from the group formed by hydroxy, amino or alkoxy groups with a maximum of 4 carbon atoms in the alkyl, carboxy or carbalkoxy moiety with a maximum of 4 carbon atoms in the alkyl residue, or the alkylamino or dialkylamino group with a maximum of 4 carbon atoms in the alkyl thereof, and can be saturated or unsaturated, especially with only one double bond.

The alcohols which esterify the carboxy functions of the N-acyl lysogangliosides according to the present invention can be monovalent or polyvalent, in particular bivalent. Of the alcohols of the aliphatic series, special mention should be made of lower alcohols with a maximum of 6 carbon atoms, such as methyl alcohol, ethyl alcohol, propyl alcohol and isopropyl alcohol, n-butyl alcohol, isobutyl alcohol, and tert-butyl alcohol, and of the bivalent alcohols, ethylene glycol and propylene glycol. Of the alcohols of the araliphatic series, should be mentioned in particular those with one single benzene ring, such as benzyl alcohol and phenethyl alcohol. Of the alcohols of the alicyclic series, preference should be given to those with only one cycloaliphatic ring, such as cyclohexanol, or terpene alcohols, such as menthanol or carvomenthol, or one of the terpineols or piperitol.

Of the alcohols of the heterocyclic series, special mention should be made of tetrahydrofuranol or tetrahydropyranol. To esterify the carboxy groups of the N-acyl-lysogangliosides it is possible to use also aliphatic alcohols substituted, for example, by amino functions, such as aminoalcohols, for example those with a maximum of 4 carbon atoms and especially aminoalcohols with a dialkyl ($C_{1-4}$) -amino group such as diethylaminoethanol.

The carboxylamide functions according to the present invention are either derived from ammonia (and the amide in this case is the unsubstituted amide —$CONH_2$) or from primary or secondary amines, especially from those containing a maximum of 12 carbon atoms. Such amines can be of an aromatic, heterocyclic or alicyclic nature, but are preferably aliphatic. Preferred objects of the present invention are the carboxylamide derivatives of aliphatic amines with a maximum of 12 carbon atoms, the amines of which can be open-chained, straight-chained or branched or they can be cyclic, such as the alkylamines derived from alkyls having from 1 to 6 carbon atoms, such as methylamine, ethylamine, propylamine, hexylamine, dimethylamine, diethylamine, di-isopropylamine, dihexylamine, or the alkyleneamines derived from alkylene groups with straight chains having from 3 to 6 carbon atoms or corresponding chains substituted by 1 to 3 methyl groups, such as pyrrolidine, piperidine and azepine. The alkyl or alkylene groups of these amines can also be interrupted in the carbon atom chain or substituted by other hetero-atoms, in particular by nitrogen atoms. The amides of the invention are derived in this case from diamines, such as ethylenediamine, trimethylenediamine or piperazine. If the alkyl or alkylene groups are interrupted or substituted by oxygen or sulphur atoms, the amides represent derivatives of aminoalcohols, such as aminoethanol or aminopropanol or are derived from morpholine or thiomorpholine.

Of special interest in terms of the present invention are the aforesaid esters and amides of N-acyl lysogangliosides derived from gangliosides of groups A and B mentioned above, and of their mixtures.

The invention also includes the derivatives peracylated in the hydroxyls of the saccharide part, sialic acids and ceramide of the esters and amides described herein. In such derivatives the acyl groups can be derived from acids of the aliphatic, aromatic, araliphatic, alicyclic or heterocyclic series. They are derived preferably from acids of the aliphatic series with a maximum of 10 carbon atoms and especially 6 carbon atoms, such as formic acid, acetic acid, propionic acid, the butyric acids, valerianic acids, capronic acid or caprinic acid. They can also be derived from acids, for example, with the same number of carbon atoms but substituted, particularly by hydroxyacids, such as lactic acid, by aminoacids such as glycine or by dibasic acids, such as succinic, malonic or maleic acid.

Of the aromatic acids should be mentioned those with only one benzene nucleus, particularly benzoic acid and its derivatives with methyl, hydroxy, amino or carboxy groups, such as p-aminobenzoic acid, salicylic acid or phthalic acid.

The invention also includes the peracylated derivatives of N-acyl lysogangliosides and their mixtures described previously, with, however, free carboxy functions. Of particular importance to these derivatives are those acylated derivatives derived from the acids listed herein. One group of new derivatives to be specially mentioned is the one constituted by gangliosides esterified or converted into amides or peracylated on the hydroxyl groups, the ester groups of which are derived from aliphatic alcohols with a maximum of 6 saturated carbon atoms, unsubstituted or substituted by hydroxy, alkoxy groups with a maximum of 4 carbon atoms, amino, alkylamino or dialkylamino groups with a maximum of 4 carbon atoms in the alkyl groups, carboxy groups, carbalkoxy groups with a maximum of 4 carbon atoms in the alkyl residue, and by the corresponding alcohols with one double bond at the most, by araliphatic alcohols with only one benzene ring, unsubstituted or substituted by 1 to 3 methyl groups, by cycloaliphatic or aliphatic-cycloaliphatic alcohols with a cyclohexane ring, unsubstituted or substituted by 1 to 3 methyl groups and a maximum of 4 carbon atoms in the aliphatic part, by tetrahydrofuranol or by tetrahydropyranol.

The amide groups therein may be derived from ammonia or from alkylamines, dialkylamines or alkyleneamines with a maximum of 6 carbon atoms in the alkyl groups and by 4 to 8 carbon atoms in the alkylene groups and in which the alkyl or alkylene groups can be interrupted in the carbon atom chain by heteroatoms chosen from the group formed by nitrogen, oxygen and sulphur, the amino group being possibly —NH— in cases where a nitrogen atom substituted by an alkyl with a maximum of 4 carbon atoms is present and/or they may be substituted by groups chosen from the group formed by amino, alkylamino or dialkylamino groups with a maximum of 4 carbon atoms in the alkyl groups, or by hydroxy or alkoxy groups with a maximum of 4 carbon atoms in the alkyl group, or by araliphatic amines with only one benzene ring, optionally substituted by a maximum of 3 methyl groups and with a maximum of 4 carbon atoms in the aliphatic part, and in which the acyl groups which esterify the hydroxyls are derived from saturated or unsaturated aliphatic acids with a maximum of 6 carbon atoms, which can also be substituted by a function chosen from the groups formed by hydroxy, amino and carboxy groups, and by their salts.

Of the functional derivatives of the new semi-synthetic ganglioside analogues should be mentioned especially the sialic esters of the aforesaid new compounds and derived from methyl, ethyl, propyl, isopropyl, n-butyl, isobutyl, tert-butyl, benzyl, allyl, ethoxycarbonylmethyl, or cyclohexyl alcohol, the sialic amides derived from methylamine, ethylamine, propylamine, dimethylamine, diethylamine, pyrrolidine, piperidine, piperazine, morpholine, or thiomorpholine, and their peracylates, perpropionylates, perbutyrylates, permaleylates, persuccinylates and the peracylated analogues of the aforesaid sialic esters and amides.

The N-acyl radicals derived from an acid of the aromatic, alicyclic or heterocyclic series can have the cyclic system directly bound to the carbamide group —NH—CO— of the neuraminic or sphingosine residues of the ganglioside derivative, or by an aliphatic, alkylene or alkylidene residue. The aforesaid terms therefore embrace, in the range of the present invention, both the derivatives of the aromatic, alicyclic or heterocyclic acids as such (that is, bound directly to the carbamide group) and the derivatives of araliphatic, aliphatic, alicyclic and aliphatic heterocyclic acid. The rings of these hydrocarbyl residues can of course in turn be substituted by aliphatic hydrocarbyl groups. The aforesaid aliphatic chains can also be interrupted by heteroatoms, for example, those chosen from the group formed by N, S and O. The cyclic systems can be mono- or polycyclic, preferably, in the second case, bicyclic. The acids can be mono or polybasic, and preferably, in the second case, dibasic.

The N-acyl radicals of the compounds of the invention possess preferably from 6 to 24carbon atoms and can contain one or more cyclic systems, preferably however only one, optionally substituted in their turn by aliphatic hydrocarbyl groups, especially alkyls, preferably with a maximum of 6 carbon atoms. The hydrocarbyl residues of the N-acyl groups can also be substituted, both in the aliphatic parts and in the rings, by functions Or modified functions, such as especially halogens, for example chlorine, bromine and fluorine, free or esterified hydroxy groups, free or esterified amino groups, or acylates, or substituted by alkyl or alkylene groups, free or catalyzed oxo-groups, oximes or substituted oximes, hydrazones or substituted hydrazones, free or etherified mercapto groups, free or substituted sulfamide groups, free or esterified sulfonic groups, sulfoxide groups or nitryl or nitro groups. The esters of the hydroxy or amino groups can be derived from acids of the aliphatic, araliphatic, alicyclic or heterocyclic series. Such ester groups are derived above all from therapeutically acceptable acids. The aliphatic acids are preferably lower acids with a maximum of 8 carbon atoms, such as acetic, propionic, butyric, or valerianic acid, for example isovalerianic acid, or their substituted derivatives such as hydroxyacids, for example glycolic acid, or α- or β-hydroxybutyric acid, lactic acid or aminoacids, for example-natural aminoacids such as glycine, alanine, valine or henylglycine, or dibasic acids, such as malonic acid, succinic acid, maleic acid or malic acid, which also may be optionally substituted.

Those of the aromatic series are, for example, benzoic acid or its derivatives substituted by 1 to 3 lower alkyl groups, hydroxy or lower alkoxy groups, or by halogens such as chlorine, bromine or fluorine. Of the araliphatic acids should be mentioned primarily those with only one benzene ring, such as phenylacetic or phenylpropionic acid, optionally substituted as previously described. Alicyclic acids are preferably those with rings of 5 or 6 carbon atoms, such as cyclohexanecarboxyl acid and cyclohexanedicarboxyl acid. Acids of the heterocyclic series are those reported hereafter, but are preferably simple acids with only one heterocyclic group, such as derivatives of pyridine, for example, nicotinic acid and isonicotinic acid or pyrrolidine-carboxyl acid.

Suitable alcohols which can represent the etherifying component of the hydroxy or mercapto etherifying groups are all those previously listed with regard to the esters of the sialic carboxy groups, being part of the acyl-lysogangliosides of the present invention in the form of their functional derivatives. Preferable are lower aliphatic or araliphatic alcohols with a maximum of 4 carbon atoms in the aliphatic part. The alkyl or aralkyl groups as substituents on the amino groups or which are present in substituted ketal, acetal or keto groups or in esterified carboxy groups preferably have a maximum of 4 carbon atoms in the aliphatic part and a benzene group optionally substituted as described previously. The same maximum number of carbon atoms is also present in all the aliphatic groups designated as "lower" in the aforesaid definitions. A lower alkylene group, which can substitute amino groups, thus forming saturated heterocyclic groups, is constituted above all by those having 4 or 5 carbon atoms.

Aromatic acyl groups are derived primarily from acids with only one aromatic ring, such as benzoic acid and its derivatives substituted by one or more, particularly by 1 to 3 groups, chosen from the group formed by alkyl, hydroxy, oxo, amino, mercapto, carboxy and sulfonic groups, free or functionally modified, or halogens, for example as described above. Examples thereof include benzoic, salicylic, p-aminobenzoic, the three isomers of toluic acid, phthalic, isophthalic or terephthalic acid, p-hydroxybenzoic, protocatechuic, anisic, vanillic, veratric, piperonylic, resorcylic, orsellinic, pyrogallic, p-sulfaminebenzoic, 2,6-dimethoxybenzoic, 3,4,5-trimethoxybenzoic, 2-chlorobenzoic, 3-chlorobenzoic, 4-chlorobenzoic, 4-acetamidebenzoic, N-acetylanthranylic, 3-amino-benzoic, 4-aminobenzoic, 2-amino-4-chlorobenzoic, 4-amino-2-chlorobenzoic, 3-amino-4-methoxybenzoic, 4-butoxybenzoic, 4-butylbenzoic, 2-chloro-5-methylthiobenzoic, 4-chlorophenoxyacetic, 4-chloro-3-sulfamoylbenzoic, 4-cyanbenzoic, 2,3-dichlorobenzoic, 2,4-dichlorobenzoic, 2,5-dichlorobenzoic, 2,6-dichlorobenzoic, 3,4-dichlorobenzoic, 3,5-dichlorobenzoic, 4-diethylaminobenzoic, 3,4-difluorobenzoic, 4-ethoxybenzoic, 2-fluorobenzoic, 4-fluorobenzoic, 4-fluorophenoxyacetic, 4-heptyl-benzoic, 2-(4-hydroxyphenoxy) propionic, 4-methylthiobenzoic, phenoxyacetic, 2-sulfobenzoic, and α-trifluoro-o-toluic acid.

These acyl groups can however also derive from acids with several benzene rings, condensed or not condensed, or with benzene rings and other cyclic hydrocarbyl residues, such as alicyclic or heterocyclic residues, such as for example, naphthoic, p-aminonaphthoic, p-hydroxynaphthoic, naphthalic, diphenyl-o,o'-dicarbonic, 3-methylindene-2-carboxy and 2-ethoxy-1-naphthoic acid.

Of the araliphatic acids there can be mentioned those with only one benzene ring, optionally substituted as described previously, and in which the aliphatic chain preferably has from 1 to 6 carbon atoms, Such acids can be straight-chained or branched, saturated or unsaturated, and can also be substituted by one of the aforesaid functions or their derivatives and/or can be interrupted by heteroatoms chosen from the group formed by N, O and S, or by other aromatic or heterocyclic or alicyclic nuclei. Specific acids of this type are, for example, phenylacetic, hydrotropic, cinnamic, phenylpropiolic, piperic, mandelic, 3-(4-fluoro-benzoyl)-propionic, α- fluorocinnamic, 4-fluorocinnamic, 3-fluoro-4-hydroxyphenylacetic, 4-fluorophenoxyacetic, α-fluorophenylacetic, 4-hydroxymandelic, (+)-6-methoxy-α-methyl-2-naphthalinacetic, 1-naphthoxyacetic, phenoxyacetic, 4-phenoxybenzoic, 3-trifluoromethylcinnamic, 4-trifluoromethylmandelic, α,α,α-trifluoro-p-tolylacetic, 3,4,5-trimethoxycinnamic, phenylglycine, D-4-hydroxyphenylglycine, α-sulfobenzeneacetic, 4-hydroxyphenylpropandioic, α-amino3,4-di-hydroxybenzeneacetic, 4-aminocinnamic, N-benzoyl-L-threonine, benzylthioglycolic, 4-bromomandelic, chloroacetyltyrosine, 2-chloro-6-fluorophenylacetic, 4-chlorophenoxyacetic, transcinnamic, 3-(4-fluorobenzoyl)-propionic, 4-fluorophenylacetic, DL-4-hydroxymandelic, 2-(4-hydroxyphenoxy)-propionic, (S)-(+)-α-methoxyphenylacetic, (R)-(+)-α-methoxy-α-(trifluoromethyl)-phenylacetic, and (S)-(−)-α-methoxy-α-(trifluoromethyl)-phenylacetic acid.

Alicyclic acyl groups are primarily derived from acids containing from 1 to 3 alicyclic rings, chosen preferably from those having 5 to 7 cyclic carbon atoms, optionally substituted by aromatic hydrocarbyl residues, for example benzene or naphthalene, or aliphatic residues, for example alkyl or alkenyl, with preferably from 1 to 6 carbon atoms, or by hydroxy, oxo, amino or carboxy groups, free or functionally modified, for example as described previously. In those groups derived from alicyclic acids as such, the carboxyl directly substitutes one or more atoms of the ring hydrogens, or it may be found in one of the aforesaid aliphatic hydrocarbyl groups, thus providing alicyclic-aliphatic acids. In this case the aliphatic chain of such alicyclic aliphatic acids can be substituted by functions such as those listed above for the case of araliphatic acids, or it can be interrupted by heteroatoms such as those mentioned previously. Acids specific to this series are, for example, cyclopropanecarboxy, cyclobutanecarboxy, cyclohexanecarboxy, 1-amino-1cyclohexanecarboxy, cyclo-pentanecarboxy, 2,2-dichloro-1-methylcyclopropane-carboxy, 1-methyl-1-cyclohexanecarboxy, 3-noradamantanecarboxy, 1-phenyl-1-cyclopropanecarboxy, (±)-1-benzocyclobutenecarboxy, (1S)-(−)-camphanic, (+)-camphorcarboxy, (−)-isoborneolacetic, (−)-menthoxy-acetic, 5-methoxy-1-indanon-3-acetic, 3-methyl-1-adamantaneacetic, 3-methylinden-2-carboxy, 2-norbornaneacetic, 1,2,3,4-tetrahydro-2-naphthoic, 1-adamantaneacetic, cycloheptanecarboxy, and cyclohexanebutyric acid.

One group of particular interest for the purposes of the present invention is comprised of steroid acids, such as for example cholic and cholanic acids, such as cholanic acid, cholic acid, lithocholic acid, deoxycholic acid and the respective ethio-acids, the ethio-acids derived from androstane or pregnane or from their unsaturated derivatives in the 4,5-position.

The heterocyclic residues of the acyls derived from acids of this series can be tricyclic or octacyclic, preferably between penta- and heptacyclic and can contain between one and four heteroatoms chosen from the group formed by O, N, and S and can be saturated or unsaturated, in particular with an aromatic system of double bonds. Moreover, they can be substituted by one or more of the groups already named with regard to the aromatic and alicyclic acyl groups. In particular they can be substituted by aliphatic hydrocarbyl groups, especially by alkyl groups with a maximum of 6 carbon atoms, which can also be interrupted in the carbon atom chain by one of the aforesaid heteroatoms. The heterocyclic groups of this class can also be substituted with aliphatic, alicyclic or araliphatic acids and in this case too the aliphatic chain can be substituted by one of the aforesaid groups, such as amino, hydroxy, free or functionally modified sulfonic or sulfamide groups, or they can be interrupted by other heteroatoms in the aforesaid manner.

Particular mention should be made of acyls derived from heterocyclic single-ringed acids, such as pyrrole, pyrazol, imidazol, thiophene, furan, pyran, pyridine, pyrimidine, pyrazine, thiopyran, oxazol, isoxazol, thiazole, isothiazole, triazols, tetrazol, triazines and those resulting from the condensation of these heterocyclics with a benzene or naphthalic ring, or with several aromatic rings of this type, such as especially indole, indolizine, coumarine, thionaphthene, carbazol, indazol, benzimidazol, benzothiazole, benzoisothiazole, quinoline, isoquinoline, acridine, phenanthridine, chromene, cinnoline, phthalazine, quinazoline, phenazine, phenoxazine, phenothiazine and benzodiazepine, and those derived from the condensation of one or more of the aforesaid heterocyclic compounds with other heterocyclics and/or with aromatic or benzene rings.

Finally, acids of the aforesaid types derived from alkaloids are to be considered. Such acids are preferably known acids of biological or therapeutic-pharmaceutical interest.

The acyls of the sphingosine and/or neuraminic groups according to the present invention can be derived from acid compounds of the aforesaid heterocyclic type, in which there are present double bonds of the aromatic type, such as in pyridine or pyrrole, or from corresponding derivatives, partially or completely hydrogenated, such as piperidine or piperazine. The following acids are specific examples of such acids: 2-furoic acid, 3-furoic acid, 2-thiopheneacetic acid, 2-amino-4-thiazolacetic acid, nicotinic acid, isonicotinic acid, picolinic acid, 7-theophyllineacetic acid, 2-aminonicotinic acid, 6-aminonicotinic acid, 5-aminoorotic acid, (S)-(−)-2-azetidincarboxy acid, 5-bromonicotinic acid, 5-chloroindol-2-carboxy acid, 6-chloronicotinic acid, cinnoline-4-carboxy acid, L-histidine, N-acetyl-L-histidine, N-acetyl-L-tryptophan, 3-amino-4pyrazolcarboxy acid, 3-amino-1,2,4-triazol-5-carboxy acid, 5-benzimidazolcarboxy acid, 2-benzofurancarboxy acid, (+)-biotin, 2-chloronicotinic acid, 2,4-dihydroxypyrimidin-5-carboxy acid, 5-fluoroindol-2carboxy acid, 2-furanpropionic acid, 5-hydantoinacetic acid, 5-hydroxyindol-3-acetic acid, 5-hydroxy-2-indolcarboxy acid, 6-hydroxynicotinic acid, 4-imidazolacetic acid, 5-methoxyindole-3-acetic acid, 5-methoxyindole-2-carboxy acid, 5-methoxy-2-methyl-3-indoleacetic acid, 4-methoxy-2-quinolinecarboxy acid, kinurenic acid, thiokinurenic acid, 7-chlorokinurenic acid, chlorothiokinurenic acids, fluorothiokinurenic acid and trifluoromethylthiokinurenic acid, 1-methylindol-2-carboxy acid, 6-methylnicotinic acid, N-methyl-L-proline acid, 1-methyl-2-pyrrolcarboxy acid, 3-methyl-2-thiophenecarboxy acid, 5-methyl-2-thiophenecarboxy acid, niflumic acid, 5-nitro-2-furoic acid, (−)-2-oxo-4-thiazolidincarboxy acid, 1-piperidinpropionic acid, 2-pyrazincarboxy acid, 4-pyrazolcarboxy acid, 4-pyridazincarboxy acid, 2-pyridylacetic acid, 3-(3-pyridyl)-acrylic acid, 4-pyridylthioacetic acid, (2-pyrimidylthio)acetic acid, quinaldicacid, 3-quinolincarboxy acid, 4-quinolincarboxy acid, 4-(2-thienyl)-butyric acid, 3-thiopheneacetic acid, 2-thiopheneacetic acid, 2-(methylthio)-nicotinic acid, pyridylthioacetic acid, tetrazol-1-acetic acid, α-oxo-2furanacetic acid, (methoxymino)-2-furanacetic acid, 2-α-(methoxymino)-4-thiazolacetic acid, α-[[(4-ethyl-2,3-dioxo-1-piperazinyl)-carbonyl]amino]-benzeneacetic acid, 1,3-dithiane-2-carboxy acid, 3-(2-chlorophenyl)-5-methyl-4-isoxazolcarboxy acid, 3-(2-chloro-6-fluoro-phenyl)-5-methyl-4-isoxazolcarboxy acid, and 3-(2,6-dichlorophenyl)-4-isoxazolcarboxy acid.

In the N- and N'-acyl-N,N'-di-lysogangliosides according to the present invention, the acyl group is one of the aforesaid groups of the aromatic, alicyclic, araliphatic or heterocyclic series. Therefore, at least one of the acyl groups, both on the sphingosine nitrogen and on the neuraminic nitrogen, must be of this nature. In the N,N'-diacyl-N,N'-di-lysogangliosides, both the acyl groups can be derived from acids of the aforesaid series and such compounds are of particular importance with regard to the present invention since they are easier to prepare.

In the N,N'-diacyl derivatives, one of the acyl groups can however also be derived from a saturated or unsaturated aliphatic acid, substituted or not substituted, preferably with from 1 to 24 carbon atoms. Of such acids can be mentioned the lower acids having from 1 to 11 carbon atoms, straight-chained or branched, such as formic acid, acetic acid, propionic acid, the butyric acids, the valerianic acids such as especially n-valerianic acid and isovalerianic acid, pivalic acid, capronic and isocapronic acid, enanthic acid, caprylic acid, pelargonic acid, caprinic and undecylic acid, di-tert-butylacetic acid, and 2-propylvalerianic acid. Of the unsaturated acids can be mentioned angelic acid and tiglic acid. Suitable longer-chained acids include those with straight chains and especially those having from 12 to 16 carbon atoms, for example lauric acid, myristic acid and palmitic acid. Those with an even higher carbon content include, for example, oleic acid, elaidinic acid, stearic acid, eicosancarbonic acid and behenic acid. In the acyl groups with branched chains, the lateral chains are preferably lower alkyls with a maximum of 4 carbon atoms, especially methyl groups.

Of particular interest are N,N'-diacyl-N,N'-dilysogangliosides in which an aliphatic acyl on the neuraminic nitrogen is a mixed acyl as is present in natural gangliosides, that is, acetyl for the most part and glycolyl for the lesser part, and wherein the hydroxyls of the neuraminic residue are also optionally acylated. Such derivatives are obtained by selective hydrolysis on the sphingosine nitrogen of gangliosides and by acylation of the N'-lysogangliosides thus obtained in the N-position with one of the aforesaid acids of the aromatic, araliphatic, alicyclic or heterocyclic series. Similarly, it is possible to selectively hydrolyze the gangliosides on the neuraminic nitrogen and in the N'-lyso-gangliosides obtained to acylate the amino group in this position with one of the aforesaid non-aliphatic acids. The mixed acyls derived from higher fatty acids, as are present in natural gangliosides, remain on the sphingosine nitrogen. This is a preferred objective of the present invention.

The aliphatic acyl groups optionally present on the neuraminic nitrogen or sphingosine nitrogen can also be substituted by free functional or functionally modified groups, preferably functional polar groups. Preferably, from 1 to 3 functional groups are present and are chosen from the group formed by hydroxy, amino, ketone, mercapto, carboxy, sulfonic, sulfamide, sulfoxide, or sulfone and nitryl or nitro groups and from the functional derivatives of these groups such as esters of hydroxy, mercapto, carboxy, sulfonic, ketal, acetal, ketoxime, aldoxy and hydrazone groups. Groups of this type may be optionally substituted with lower aliphatic or araliphatic hydrocarbyl groups having from 1 to 6 carbon atoms in the aliphatic part and preferably only one benzene ring, such as alkylamine, alkyleneamine, alkylmercapto, alkylsulfamide and alkylhydrazone groups. Of the esters of hydroxyl groups can be mentioned particularly those of the inorganic hydracids, that is halogens, particularly chlorine, fluorine and bromine.

Of particular importance among the new acyl-di-lysogangliosides of the invention are the N-acyl-N-lysogangliosides derived from natural gangliosides, such as the gangliosides $GM_1$, $GD_{1a}$, $GD_{1b}$, $GT_{1b}$, $GM_2$ and $GM_3$. In such derivatives the neuraminic acyl groups are those which are present in such gangliosides, i.e., a mixed acetyl-glycol group, the acetyl group being prevalent, and in which the sialic hydroxy groups are optionally esterified with the corresponding acids. They are obtained from gangliosides by enzymatic hydrolysis involving a deacylation on the sphingosine nitrogen alone and by subsequent acylation with an aromatic, araliphatic, alicyclic or heterocyclic acid. The following are examples of such compounds:

N-2,6-dimethoxybenzoyl-N-lyso $GM_1$
N-5-methoxy-indanon-3-acetyl-N-lyso $GM_1$
N-phenylacetyl-N-lyso $GM_1$
N-cyclobutanecarbonyl-N-lyso $GM_1$
N-2-norbornaneacetyl-N-lyso $GM_1$
N-furoyl-N-lyso $GM_1$
N-imidazolacetyl-$GM_1$
N-6-methylnicotinyl-N-lyso $GM_1$
N-methylprolyl-N-lyso $GM_1$
N-1-methyl-2-pyrrolcarbonyl-N-lyso $GM_1$
N-2-pyridylacetyl-N-lyso $GM_1$
N-4,4-pyridylthioacetyl-N-lyso $GM_1$
N-3-quinolincarbonyl-N-lyso $GM_1$
N-tetrazolyl-1-acetyl-N-lyso $GM_1$
N-7-theophyllineacetyl-N-lyso $GM_1$
N-2-thiophenacetyl-N-lyso $GM_1$
N-3-amino-1,2,4,-triazol-5-acetyl-N-lyso $GM_1$
N-acetyl-DL-tryptophenacetyl-(α, α, α-trifluorotoluidin)-nicotinyl-$GM_1$
N-5-hydantoinacetyl-N-lyso $GM_1$
N-5-hydroxyindol-3-acetyl-N-lyso $GM_1$
N-2-chloronicotinyl-N-lyso $GM_1$
N-5-methyl-2-thiophenacetyl-N-lyso $GM_1$
N-5-benzimidazolacetyl-N-lyso $GM_1$
N-5-hydroxy-2-indolacetyl-N-lyso $GM_1$
N-3,4,5-trimethoxybenzoyl-N-lyso $GM_1$
N-cycloheptaneacetyl-N-lyso $GM_1$
N-cyclopentaneacetyl-N-lyso $GM_1$
N-5-methyl-2-thiophenacetyl-lyso $GM_1$ and the corresponding derivatives of the other basic gangliosides named previously and the inner esters of all of these compounds.

Examples of N,N'-diacyl-N,N'-di-lysogangliosides are the derivatives corresponding to the aforesaid N-acyl-N-lysogangliosides derived from $GM_1$ gangliosides or the other gangliosides, previously named, in which the amino group on the neuraminic nitrogen is also acylated with the same acids, for example N,N'-di-cycloheptylacetyl-N,N'-di-lyso $GM_1$, N,N'-di-cyclopentylcarboxyl-N,N'-di-lyso GM$_1$, N,N'-di-phenylacetyl-N,N'-dilyso GM$_1$, N,N'-di-pyridylacetyl-N,N'-di-lyso GM$_1$ or N,N'-di(5-methyl-2-thiophenacetyl)-di-lyso GM$_1$.

Examples of N'-monoacyl-N,N'-di-lysogangliosides derived from the ganglioside GM$_1$ and from the other basic gangliosides named herein contain the acyl groups which were mentioned in the examples specific to GM$_1$N-mono-lysogangliosides on the neuraminic nitrogen instead of on the sphingosine nitrogen. Another interesting group of compounds according to the present invention are for example the ganglioside derivatives corresponding to the aforesaid N-acyl-N-lyso GM$_1$ compounds in which the "natural" mixed acyl on the neuraminic nitrogen is substituted by an aliphatic acid with between 3 and 6 carbon atoms, such as valerianic or pivalic acid, or an acid of this type substituted with halogens, that is, monochloroacetic or dichloroacetic acid, or an aliphatic acid with between 12 and 18 carbon atoms such as palmitic, oleic or stearic acid.

Of the compounds with functionally modified sialic carboxy functions can be mentioned the esters derived from lower aliphatic alcohols having from 1 to 6 carbon atoms, such as methyl, ethyl or propyl esters, the amides derived from lower aliphatic amines, such as methylamine, ethylamine or propylamine or cyclic amines, such as piperidine or piperazine, pyrrolidine, the inner esters and the peracylates, peracetylates, perpropionylates, and perbutyrlates (that is, acylates derived from aliphatic acids having from 1 to 6 carbon atoms) of all the aforesaid specific compounds. The semisynthetic ganglioside analogues of the present invention can be prepared in the known way, by acylating the di-lysogangliosides or their N-acyl or N'-acyl derivatives, or optionally selectively deacylating the N,N'-diacyl-N,N'-di-lysogangliosides on the sphingosine nitrogen and on the neuraminic nitrogen.

tained from gangliosides or from N-lysogangliosides by alkaline hydrolysis, for example with hydroxides of tetraalkylammonium, potassium hydroxide and others. To prepare products according to the invention in which the acylamino groups are derived from different acids, it is preferable to use as starting compounds the N- or the N'-monoacyl derivatives of di-lysogangliosides. The N-mono-acyl-di-lysogangliosides can be obtained by selective acylation from di-lysogangliosides, since the sphingosine amino group is more reactive than the neuraminic amino. Mild acylation of the dilysogangliosides according to known methods, for example by the acylation methods used in peptide chemistry, makes it possible to obtain the aforesaid monoacyl derivatives on the sphingosine nitrogen. This is followed by acylation on the neuraminic nitrogen in the conventional manner. The acylation procedure to obtain the products according to the invention consists in this case in a two-step acylation reaction.

Various methods can be used to prepare compounds with monoacyls derived on the neuraminic nitrogen. It is possible, for example, to start from di-lysogangliosides and proceed to perform intermediate provisional protection of the sphingosine amino group, for example by hydrophobic interaction with phosphatidylcholine, or by acylation with suitable protecting groups, subsequent acylation on the neuraminic nitrogen with a derivative of the acid to be introduced in this position, then deprotection on the sphingosine nitrogen. It is also possible to acylate the di-lysogangliosides on the two amino groups with the same acid and then expose the diacyl compound to the action of enzymes capable of selectively splitting only the acylamino group on the sphingosine nitrogen, for example with enzymes used to obtain the lysogangliosides from gangliosides. An example is the glycosphingolipid-ceramide-deacylase enzyme (see Scheme 1).

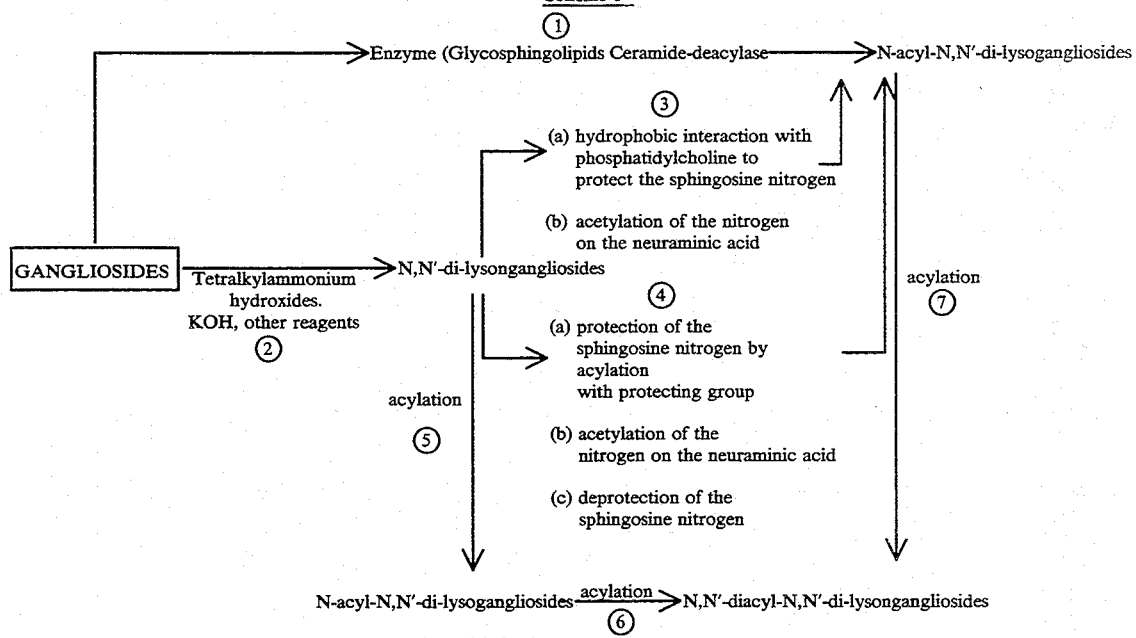

In order to prepare di-acyl derivatives in which the acylamino groups are derived from the same acid, it is preferable, for the sake of simplicity, to acylate the di-lysogangliosides in one single operation by the known procedures. The di-lysogangliosides can be ob- N-monoacyl-N,N'-di-lysogangliosides can however also be obtained by deacylation of N,N'-diacyl-N,N'-dilysogangliosides on the neuraminic nitrogen by selective chemical hydrolysis, for example with 0.1 molar alcoholic potassium hydroxide.

In the acyl-di-lysogangliosides obtained, it is possible, if desired, to functionally convert the carboxy groups of the sialic acids or hydroxyls of such acids. For example, these groups may be converted into esters or amides or the hydroxyls in these groups may be esterified with acids (peracylates).

The procedure for the preparation of N-acyl-N,N'-di-lyso-gangliosides, N'-acyl-N,N'-di-lysogangliosides and N,N'-diacyl-N,N'-di-lysogangliosides according to the present invention comprises acylating the N,N'-dilysogangliosides, N-acyl-N,N'-dilysogangliosides or N'-acyl-N,N'-di-lysogangliosides with the acids corresponding to the aforesaid acyl groups or deacylating the suitable N,N'-diacyl-N,N'-diacyl-N,N'-dilysogangliosides selectively on the sphingosine nitrogen or on the neuraminic nitrogen, or mixtures of these compounds. If desired, the compounds obtained may be converted into esters, amides or inner esters or into hydroxy peracylates. Such compounds may also be converted into suitable salts.

The N-acylation according to the aforesaid procedure can be effected in the conventional manner, for example by reacting the starting products with an acylating agent, and above all with a functional derivative of the acid, the residue of which is to be introduced. Thus, it is possible to use as the functional derivative of the acid a halogenide or an anhydride and acylation is then performed preferably in the presence of a tertiary base, such as pyridine or collidine. It is possible to operate under anhydrous conditions, at room temperature or higher or also, to advantage, according to the method of Schotten-Baumann under aqueous conditions in the presence of an inorganic base. In some cases it is possible to also use the esters of the acids as reactive functional derivatives. To acylate, it is possible to use methods with activated carboxy derivatives, such as are used in peptide chemistry, for example the method with mixed anhydrides or derivatives obtainable with derivatives of carbodiimides or the salts of isoxazolium. Of the various preparation methods, the most appropriate are the following:

1. Reaction of the lysoganglioside derivative with the azide of the acid;
2. Reaction of the lysoganglioside derivative with an acylimidazole of the acid obtainable from the acid with N,N'-carbonyldiimidazole;
3. Reaction of the lysoganglioside derivative with a mixed anhydride of the acid and trifluoroacetic acid;
4. Reaction of the lysoganglioside derivative with the acid chloride;
5. Reaction of the lysoganglioside derivative with the acid in the presence of a carbodiimide (such as dicyclohexylcarbodiimide) and optionally of a substance such as 1-hydroxy-benzotriazol;
6. Reaction of the lysoganglioside derivative with the acid by heating;
7. Reaction of the lysoganglioside derivative with a methyl ester of the acid at a high temperature;
8. Reaction of the lysoganglioside derivative with a phenol ester of the acid, such as an ester with para-nitrophenol; and
9. Reaction of the lysoganglioside derivative with an ester derived from the exchange between a salt of the acid and 1-methyl-2-chloropyridinium iodide.

It has already been noted how it is possible to obtain selective partial acylation both on the sphingosine nitrogen and on the neuraminic nitrogen. Scheme 1 illustrates the procedures.

Enzymatic deacylation of N,N'-diacyl-N,N'-dilysogangliosides on the sphingosine nitrogen as reported previously can be carried out under the conditions used for the partial deacylation of gangliosides, for example as described in J. Biochem., 103, 1 (1988). The double deacylation of N,N'-diacyl-N,N'-di-lysoganglio-sides to N,N'-di-lysogangliosides can be effected in the same way as for the preparation of de-N-acetyl-lysogangliosides as described for example in Biochemistry 24, 525 (1985); J. Biol. Chem. 255, 7657, (1980); Biol. Chem. Hoppe Seyler 367, 241, (1986); Carbohydr. Research 179, 393 (1988); Bioch. Bioph. Res. Comn. 147, 127 (1987).

The aforesaid publication in Carbohydr. Research 179 also describes a method for the selective deacylation on the neuraminic nitrogen obtainable by the action of KOH 0.1M in 90% n-butanol of the ganglioside $GM_3$. This deacylation can be applied to N,N'-diacyl-N,N'-dilysogangliosides of the present invention to obtain N-acyl-N,N'-di-lysogangliosides. Of course, the preparation methods coming within the scope of the present invention also include any chemical equivalents apparent to one skilled in the art.

The preparation of carboxy or hydroxy derivatives of the novel acyl lysogangliosides obtained according to the aforesaid procedure can be effected by the known procedures, except those methods which would have the effect of altering the basic ganglioside structure. This would exclude methods that employ highly acidic agents, or which would however be carried out under drastically alkaline or acid conditions, or also those methods which would lead to an undesired alkylation of the hydroxy groups of the saccharide part.

The esterification of carboxy groups of the N-acyl gangliosides or their conversion into amides can be effected for example as described in U.S. Pat. No. 4,713,374 for gangliosides. The formation of inner esters of the derivatives of the invention can be effected as in the case of the preparation of inner esters of gangliosides, as described for example in U.S. Pat. No. 4,593,091 and in EP patent 0072 722.

These inner esters include not only the compounds formed by lactonization of sialic carboxy groups with saccharide hydroxyls, but also those for example which contain lactone rings formed between the sialic carboxyls and the sialic hydroxyls, since the latter are in turn bound to the saccharide part, and also other possible lactone structures. The procedure of the aforesaid patents for the formation of inner esters comprises treating a ganglioside in a non-aqueous organic solvent under anhydrous conditions with a lactonizing agent. Suitable organic solvents include dimethylsulfoxide, dimethylformamide, sulfolane, tetrahydrofuran, dimethoxyethane, pyridine or mixtures of these solvents. Suitable reagents for lactonization include carbodiimides soluble in organic solvents, such as dicyclohexylcarbodiimide, benzylisopropylcarbodiimide, benzylethylcarbodiimide, salts of 2-chloromethylpyridine, ethoxyacetylene and Woodward's reagent (N-ethyl-5-phenylisoxazolium-3'-sulfonate). Older methods make use of the reaction between a ganglioside and acetic acid or trichloroacetic acid or a carbodiimide, soluble in water or in an aqueous medium. All these methods can also be used to prepare inner esters of the new N-acyl lysogangliosides. For the "outer" esterification of carboxy groups, that is, esterification with alcohols of the aforesaid series, it is possible for example to react the N-acyl lysogangliosides with the desired alcohol, in the presence of an ion exchanger, e.g. a Dowex 50-type resin, the yield being limited by the simultaneous formation of inner esters and the reaction times being rather long. Another method of esterification comprises passing the alcohol on a resin, of the Dowex -50Wx8 (100–200 mesh form H) type, and treating the dissolved eluate in the same alcohol with the corresponding diazoalkane.

Another suitable ester preparation method comprises treating a metal salt of the lysoganglioside derivative with an etherifying agent. Alkaline and alkaline earth metal salts may be used, but also any other metal salt. As etherifying agents it is possible to use those reported in the literature, such as especially the esters of various inorganic acids, or of organic sulfonic acids, such as hydracids, that is, in other words, the hydrocarbyl halogenides, such as methyl or ethyl iodide etc., or the neutral sulfates or acids of hydrocarbyls, sulfites, carbonates, silicates, phosphites or hydrocarbyl sulfonates, for example methyl benzo- or ptoluolsulfonate. The reaction can be effected in a suitable solvent, for example an alcohol, preferably the one which corresponds to the alkyl group to be introduced, but also in non-polar solvents, such as ketones or ethers, such as dioxane or dimethylsulfoxide. One particularly advantageous method of esterification comprises treating an inner ester of the lysoganglioside derivative with a mixture of the desired alcohol and its corresponding alcoholate. The reaction can be conducted at a temperature corresponding to the boiling point of the alcohol, but it is also possible to use lower temperatures, the reaction times in this case being longer.

The amides of the lysoganglioside derivatives of the present invention can be prepared by known methods, and especially by the following:

(a) Reaction of the inner esters of the N-acyl lysoganglioside derivatives with ammonia or with the amines;
(b) Reaction of the carboxy esters of the N-acyl lysoganglioside derivatives with ammonia or with the amines; and
(c) Reaction of the N-acyl lysoganglioside derivatives with the carboxy groups activated with ammonia or with the amines.

Reaction (a) can be effected by direct treatment, with or without solvent, of the ganglioside inner ester with ammonia or with the amine of which the amide is to be prepared. The reaction can be effected also at quite low temperatures, such as −5° to +10°, but preferably at room temperature or higher, for example between 30° and 120°. As solvents, it is possible to use ketones, aromatic hydrocarbides, dimethylformamide, dimethylsulfoxide, dioxane or tetrahydrofuran. Reaction (b) is preferably effected under the conditions described for reaction (a). Apart from the esters described for the present invention, it is possible to also use other esters, for example esters with phenols.

To activate the carboxy group in the reaction according to (c), methods known in the field of peptide chemistry may be employed, avoiding those which involve conditions that are too acidic or basic, which could lead to the disintegration of the ganglioside molecule. If the starting gangliosides are in the form of, for example, sodium salts, it is advisable to first treat the salt with an ion exchange resin, Dowex-type, or another acid ion exchanger. It is possible to use the method of condensation in the presence of carbodiimides, for example dicyclohexylcarbodiimide, benzylisopropylcarbodiimide or benzylethylcarbodiimide, in the presence of 1-hydroxybenzotriazol or condensation in the presence of N,N'-carbonyldiimidazol.

Acylation of the hydroxy groups of the saccharide, sialic part and optionally of the ceramide residue can also be carried out in the known way, for example by acylation with a halogenide or an anhydride of the acid to be used for acylation, preferably in the presence of a tertiary base, such as pyridine or collidine. As a result, the aforesaid peracylated derivatives are obtained. It is also possible, according to the definition of the procedure of the present invention, to expose to acylation a de-N-acetyl lysoganglioside and to recover the acetylamino group in the neuraminic acid after acylation. Such acetylation can also be effected in the known way. In this case relatively mild methods are chosen for the N-acylation, by which the hydroxy group of the neuraminic acid remains unaltered. Acetylation of this group, to be effected after the acylation reaction on the sphingosine nitrogen, can be done by drastic methods, for example, by using acetic anhydride.

Finally, as noted above, in all the compounds obtainable by the aforesaid procedure which present salifiable groups, it is possible to salify such groups in the known way to obtain appropriate salt derivatives.

The invention also includes modifications of the preparation procedure of the new derivatives, in which a procedure is interrupted at any one stage or is started with an intermediate compound and the remaining steps are performed, or in which the starting products are formed in situ.

Also included in the present invention are pharmaceutical preparations which contain as active substances one or more of the new acyl lysoganglioside derivatives and, in particular, those mentioned herein. The pharmaceutical preparations mentioned herein can be preparations for oral, rectal, parenteral, local or transdermal use. They are therefore in solid or semisolid form, for example pills, tablets, gelatinous capsules, capsules, suppositories, and soft gelatin capsules. For parenteral use it is possible to use forms designed for intramuscular, subcutaneous or transdermal administration, or which are suitable for infusions or intravenous injections. These preparations can therefore be in the form of solutions of the active compounds or as freeze-dried powders of the active compounds to be mixed with one or more pharmaceutically acceptable excipients or diluents, convenient for the aforesaid uses and with an osmolarity that is compatible with the physiological fluids. For local use, preparations in the form of sprays, for example nasal sprays, creams or ointments for topical use or suitably prepared plasters for transdermal use can be used.

The preparations of the invention can be administered to humans or animals. They contain preferably from 0.01% to 10% by weight of the active compound for solutions, sprays, ointments and creams and from 1% to 100% and preferably from 5% to 50% by weight of active compound for preparations in solid form. The dosage to be administered depends on individual indications, on the desired effect and on the chosen administration route. Another feature of the present invention is represented by the therapeutic use both of the new acyllysogangliosides and of those which are already known and listed previously. This therapeutic use includes all of the previously listed indications. The daily dosages to man by injection (subcutaneous or intramuscular) or transdermal or oral administration vary between 0.05 mg to 5 mg of active substance per kg of body weight. The following Examples illustrate the preparation of the acyl-lysogangliosides of the present invention and the pharmaceutical preparations containing them as active ingredients, and their therapeutic uses. These Examples are merely illustrative and are not to be considered as limiting of the present invention.

EXAMPLE 1

N,N'-di-lyso $GM_1$ 10 g of $GM_1$ are dissolved in 200 ml KOH 3N and hydrolysis is effected for 72 hrs at 90° C.

The solution is then cooled and brought to pH 6.5 with hydrochloric acid. It is left to stand for 18 hrs at 4° C. and then the precipitated fatty acids are filtered away. The resulting solution is dialyzed against water and concentrated to 500 ml and precipitated in 5 liters (lt) of acetone.

The product is dried and high performance silica gel chromatography is effected using as eluent a mixture of chloroform/methanol/$NH_3$ 5N (55:45:10). The fractions containing the product are dried and then redissolved in water. It is brought to pH 10 with NaOH 0.01N and dialyzed, concentrated to 100 mg/ml and precipitated in 5 volumes of acetone. Yield of N,N'-di-lyso $GM_1$ is 5.7 g (70% theoretical). Silica gel chromatography with a solvent formed by chloroform/methanol/$NH_3$ 5N (55:45:10) shows the product to be a unitary compound with Rf=0.05 ($GM_1$=0.35).

EXAMPLE 2

N-lyso $GM_1$ 10 g (6.37 mM) of $GM_1$ are dissolved in 200 ml KOH 3N and hydrolysis is effected for 72 hrs at 90° C. The solution is then cooled and brought to pH 6.5 with hydrochloric acid. It is left to stand for 18 hrs at 4° C. and then the precipitated fatty acids are filtered away. It is dialyzed against water and concentrated to 500 ml and precipitated in 5 liters of acetone.

The product containing N'-lyso $GM_1$ and N,N'-dilyso $GM_1$ (20%) is vacuum-dried and then redissolved in 100 ml of dimethylformamide. 2.15 g (6.37 mM) of 9-fluorenylmethyloxycarbonyl-N-hydroxysuccinimide dissolved in 20 ml of tetrahydrofuran are then slowly added and left to react for 1 hr at room temperature. Thereafter, 3 ml (31.85 mM) of acetic anhydride and 0.9 ml (63.7 mM) of triethylamine are added. After 30 minutes, 12.5 ml of piperidine are added to remove the protecting group. The mixture is left to react for 18 hrs at room temperature and precipitated in 2 liters of acetone and dried. The material thus obtained is dissolved in $Na_2CO_3$ 1M and kept at 60° C. for 1 hr. It is dialyzed, concentrated to 100 mg/ml and precipitated in 5 volumes of acetone.

The product is passed through an S Sepharose column ($H^+$ form) equilibrated in methanol. It is washed with methanol and N-lyso $GM_1$ by eluting with $NH_4Cl$ 10 mM in methanol. The fractions containing the product are dried and then redissolved in water. The solution is brought to pH 10 with NaOH 0.01N and dialyzed, concentrated to 100 mg/ml and precipitated in 5 volumes of acetone.

Product obtained: approximately 5 g (60% theoretical).

Silica gel chromatography with a solvent formed by chloroform/methanol/$NH_3$ 5N (55:45:10) shows the product to be unitary with Rf=0.11.

EXAMPLE 3

N-cyclobutanecarbonyl-N-lyso $GM_1$ 500 mg (0.38 mM) of Lyso $GM_1$ (prepared according to Example 2) are dissolved in 1 ml of dimethylformamide, and 1.050 ml (7.6 mM) of triethylamine and 728 μl (7.6 mM) of cyclobutanecarbonyl chloride are added at room temperature.

The condensation reaction is conducted at room temperature for 4 hrs. At the end of the reaction, the solution is precipitated in 10 ml of ethyl acetate saturated with water, filtered and vacuum-dried. The product is then purified by silica gel chromatography using as eluent a mixture of chloroform/methanol/water (60:35:8).

The pure fractions are pooled, evaporated, treated with $Na_2CO_3$ 1N, dialyzed against distilled water and then concentrated to 5 ml, and precipitated in 50 ml of acetone.

Product obtained: 350 mg (66% theoretical).

Silica gel chromatography with a solvent formed by chloroform/methanol/$CaCl_2$ 0.3% (50:42:11), shows the compound to be unitary with Rf=0.33 ($GM_1$=0.43; Lyso $GM_1$=0.24).

EXAMPLE 4

N-(2-norbornaneacetyl)-N-lyso $GM_1$ 500 mg (0.38 mM) of Lyso $GM_1$ (prepared according to Example 2) are dissolved in 2.5 ml of dimethylformamide and then are added, at 0° C., 106 μl (0.76 mM) of triethylamine and norbornaneacetic anhydride freshly prepared by reacting 1.1 ml (7.6 mM) of 2-norbornaneacetic acid and 939 mg (9.12 mM) of dicyclohexylcarbodiimide dissolved in 20 ml of tetrahydrofuran and after filtering, 2 hrs later, the dicyclohexylurea which has formed.

The condensation reaction is conducted at 0° C. for 18 hrs under stirring. At the end of the reaction, the solution is concentrated to 1 ml, precipitated in 10 ml of acetone and vacuum-dried.

The product is then purified by silica gel chromatography using as eluent a mixture of chloroform/methanol/water (60:35:8).

The pure fractions are pooled, evaporated, treated with $Na_2CO_3$ 1N, dialyzed against distilled water and then concentrated to 5 ml and precipitated in 50 ml of acetone.

Product obtained: 508 mg (92% theoretical).

Silica gel chromatography with a solvent formed by chloroform/methanol/$CaCl_2$ 0.3% (50:42:11), shows the compound to be unitary with Rf=0.33 ($GM_1$=0.43; Lyso $GM_1$=0.24).

EXAMPLE 5

N-phenylacetyl-N-lyso $GM_1$ 500 mg (0.38 mM) of Lyso $GM_1$ (prepared according to Example 2) are dissolved in 2.5 ml of dimethylformamide after which are added, at room temperature, 528 μl (7.6 mM) of triethylamine, 260 mg (1.9 mM) of phenylacetic acid and 194.2 mg (0.76 mM) of 1- methyl-2-chloropyridinium iodide dissolved in 2.5 ml of dimethylformamide.

The mixture is left to react for 18 hrs at room temperature and then precipitated in 100 ml of acetone. It is filtered and dried. The product is then purified by silica gel chromatography using as eluent a mixture of chloroform/methanol/water (60:35:8).

The pure fractions are pooled, evaporated, treated with $Na_2CO_3$ 1N, dialyzed against distilled water and then concentrated to 5 ml and precipitated in 50 ml of acetone.

Product obtained: 354 mg (65% theoretical).

Silica gel chromatography with a solvent formed by chloroform/methanol/$CaCl_2$ 0.3% (50:42:11), shows the compound to be unitary with Rf=0.37 ($GM_1$=0.43; Lyso $GM_1$=0.24) and with a fluorometric reading of 254 nm.

EXAMPLE 6

N-(2,6-dimethoxybenzoyl)-N-lyso $GM_1$ 500 mg (0.38 mM) of lyso $GM_1$ (prepared according to Example 2) are dissolved in 1 ml of dimethylformamide, and then are added at room temperature 1,056 ml (7.6 mM) of triethylamine and dimethoxybenzoic anhydride freshly prepared by reacting 2.76 g (15.2 mM) of 2,6-dimethoxybenzoic acid and 1.08 g (3.8 mM) of 1-methyl-2-fluoropyridinium p-toluenesulfonate in 10 ml of dimethylformamide/tetrahydrofuran 1:1.

The condensation reaction is conducted at room temperature for 4 hrs under stirring. At the end of the reaction, the solution is concentrated to 5 ml, precipitated in 50 ml of acetone, filtered and vacuum-dried. Silica gel chromatography is effected, using as eluent a mixture of chloroform/methanol/water (60:35:8). The pure fractions are pooled, evaporated, gathered with $Na_2CO_3$ 1N, dialyzed against distilled water and then concentrated to 5 ml and precipitated in 50 ml of acetone.

Product obtained: 506 mg (90% theoretical).

Silica gel chromatography with a solvent formed by chloroform/methanol/$CaCl_2$ 0.3% (50:42:11), shows the compound to be unitary with Rf=0.35 ($GM_1$=0.43; Lyso $GM_1$=0.24) and with a fluorometric reading of 254 nm.

EXAMPLE 7

N-(2-furoyl)-N-lyso $GM_1$ 500 mg (0.38 mM) of Lyso $GM_1$ (prepared according to Example 2) are dissolved in 2.5 ml of dimethylformamide, after which are added, at room temperature, 528 μl (3.8 mM) of triethylamine, 210 mg (1.9 mM) of 2-furoic acid and 194.2 mg (0.76 mM) of 1-methyl-2-chloropyridinium iodide dissolved in 2.5 ml of dimethylformamide.

The mixture is left to react for 18 hrs at room temperature and then precipitated in 10 ml of acetone. It is filtered and dried. The product is then purified by silica gel chromatography using as eluent a mixture of chloroform/methanol/water (60:35:8). The pure fractions are pooled, evaporated, treated with $Na_2CO_3$ 1N, dialyzed against distilled water and then concentrated to 5 ml and precipitated in 50 ml of acetone.

Product obtained: 402 mg (75% theoretical).

Silica gel chromatography with a solvent formed by chloroform/methanol/$CaCl_2$ 0.3% (50:42:11), shows the compound to be unitary with Rf=0.37 ($GM_1$=0.43; Lyso $GM_1$=0.24) and with a fluorometric reading of 254 nm.

EXAMPLE 8

N-(4-imidazolacetyl)-N-lyso $GM_1$ 500 mg (0.38 mM) of Lyso $GM_1$ (prepared according to Example 2) are dissolved in 2.5 ml of dimethylformamide, after which are added, at room temperature, 1056 μl (7.6 mM) of triethylamine, 310 mg (1.9 mM) of 4-imidazolacetic acid hydrochloride and 194.2 mg (0.76 mM) of 1-methyl-2-chloropyridinium iodide dissolved in 2.5 ml of dimethylformamide. It is left to react for 18 hrs at room temperature and then precipitated in 100 ml of acetone, filtered and dried. The product is then purified by silica gel chromatography using as eluent a mixture of chloroform/methanol/water (60:35:8). The pure fractions are pooled, evaporated, treated with $Na_2CO_3$ 1N, dialyzed against distilled water and then concentrated to 5 ml and precipitated in 50 ml of acetone.

Product obtained: 352 mg (65% theoretical).

Silica gel chromatography with a solvent formed by chloroform/methanol/$CaCl_2$ 0.3% (50:42:11), shows the compound to be unitary with Rf=0.33 ($GM_1$=0.43; Lyso $GM_1$=0.24).

EXAMPLE 9

N-(1-methylprolyl)-N-lyso $GM_1$ 500 mg (0.38 mM) of Lyso $GM_1$ (prepared according to Example 2) are dissolved in 3.5 ml of dimethylformamide/water 2.5:1 after which are added, at room temperature, 1056 μl (7.6 mM) of triethylamine, 260 mg (1.9 mM) of N-methyl-L-proline and 194.2 mg (0.76 mM) of 1-methyl-2-chloropyridinium iodide dissolved in 2.5 ml of dimethylformamide. The mixture is left to react for 18 hrs at room temperature and then precipitated in 100 ml of acetone, filtered and dried. The product is then purified by silica gel chromatography using as eluent a mixture of chloroform/methanol/water (60:35:8). The pure fractions are pooled, evaporated, treated with $Na_2CO_3$ 1N, dialyzed against distilled water and then concentrated to 5 ml and precipitated in 50 ml of acetone.

Product obtained: 380 mg (70% theoretical).

Silica gel chromatography with a solvent formed by chloroform/methanol/$CaCl_2$ 0.3% (50:42:11), shows the compound to be unitary with Rf=0.33 ($GM_1$=0.43; Lyso $GM_1$=0.24).

EXAMPLE 10

N-(1-methyl-2-pyrrolecarbonyl)-N-lyso $GM_1$ 500 mg (0.38 mM) of Lyso $GM_1$ (prepared according to Example 2) are dissolved in 2.5 ml of dimethylformamide after which are added, at room temperature, 528 μl (7.6 mM) of triethylamine, 220 mg (1.9 mM) of 1-methyl-2-pyrrolecarboxy acid and 194.2 mg (0.76 mM) of 1-methyl-2-chloropyridinium iodide dissolved in 2.5 ml of dimethylformamide.

It is left to react for 18 hrs at room temperature and then precipitated in 100 ml of acetone. The reaction mixture is filtered and dried. The product is then purified by silica gel chromatography using as eluent a mixture of chloroform/methanol/water (60:35:8). The pure fractions are pooled, evaporated, treated with $Nahd_2CO_3$ 1N, dialyzed against distilled water and then concentrated to 5 ml and precipitated in 50 ml of acetone.

Product obtained: 487 mg (90% theoretical).

EXAMPLE 11

N-(1-tetrazolacetyl)-N-lyso GM$_1$ 500 mg (0.38 mM) of Lyso GM$_1$ (prepared according to Example 2) are dissolved in 2.5 ml of dimethylformamide after which are added, at room temperature, 528 µl (7.6 mM) of triethylamine, 250 mg (1.9 mM) of 1-tetrazolacetic acid and 194.2 mg (0.76 mM) of 1-methyl-2-chloropyridinium iodide dissolved in 2.5 ml of dimethylformamide.

The mixture is left to react for 18 hrs at room temperature and then precipitated in 100 ml of acetone. It is filtered and dried. The product is then purified by silica gel chromatography using as eluent a mixture of chloroform/methanol/water (60:35:8). The pure fractions are pooled, evaporated, treated with Na$_2$CO$_3$ 1N, dialyzed against distilled water and then concentrated to 5 ml and precipitated in 50 ml of acetone.

Product obtained: 472 mg (87% theoretical).

Silica gel chromatography with a solvent formed by chloroform/methanol/CaCl$_2$ 0.3% (50:42:11), shows the compound to be unitary with Rf=0.32 (GM$_1$=0.43; Lyso GM$_1$=0.24).

EXAMPLE 12

N-(2-thiopheneacetyl)-N-lyso GM$_1$ 500 mg (0.38 mM) of Lyso GM$_1$ (prepared according to Example 2) are dissolved in 2.5 ml of dimethylformamide after which are added, at room temperature, 528 µl (7.6 mM) of triethylamine, 270 mg (1.9 mM) of 2-thiopheneacetic acid and 194.2 mg (0.76 mM) of 1-methyl-2-chloropyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water (60:35:8). The pure fractions are pooled, evaporated, treated with Na$_2$CO$_3$ 1N, dialyzed against distilled water and then concentrated to 5 ml and precipitated in 50 ml of acetone.

Product obtained: 383 mg (70% theoretical).

Silica gel chromatography with a solvent formed by chloroform/methanol/CaCl$_2$ 0.3% (50: 42: 11), shows the compound to be unitary with Rf=0.34 (GM$_1$=0.43; Lyso GM$_1$=0.24) and with a fluorometric reading of 254 nm.

EXAMPLE 13

N-(6-methylnicotinoyl)-N-lyso GM$_1$ 500 mg (0.38 mM) of Lyso GM$_1$ (prepared according to Example 2) are dissolved in 2.5 ml of dimethylformamide after which are added, at room temperature, 528 µl (7.6 mM) of triethylamine, 260 mg (1.9 mM) of 6-methylnicotinic acid and 194.2 mg (0.76 mM) of 1-methyl-2-chloropyridinium iodide dissolved in 2.5 ml of dimethylformamide.

The mixture is left to react for 18 hrs at room temperature and then precipitated in 100 ml of acetone. It is filtered and dried. The product is then purified by silica gel chromatography using as eluent a mixture of chloroform/methanol/water (60:35:8).

The pure fractions are pooled, evaporated, treated with Na$_2$CO$_3$ 1N, dialyzed against distilled water and then concentrated to 5 ml and precipitated in 50 ml of acetone.

Product obtained: 218 mg (40% theoretical).

Silica gel chromatography with a solvent formed by chloroform/methanol/CaCl$_2$ 0.3% (50:42:11), shows the compound to be unitary with Rf=0.38 (GM$_1$=0.43; Lyso GM$_1$=0.24) and with a fluorometric reading of 254 nm.

EXAMPLE 14

N-(2-pyridylacetyl)-N-lyso GM$_1$ 500 mg (0.38 mM) of Lyso GM$_1$ (prepared according to Example 2) are dissolved in 3.5 ml of dimethylformamide/water 2.5:1 after which are added, at room temperature, 1056 µl (7.6 mM) of triethylamine, 330 mg (1.9 mM) of 2-pyridyl-acetic acid hydrochloride and 194.2 mg (0.76 mM) of 1-methyl-2-chloropyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water (60:35:8). The pure fractions are pooled, evaporated, treated with Nahd 2CO$_3$ 1N, dialyzed against distilled water and then concentrated to 5 ml and precipitated in 50 ml of acetone.

Product obtained: 327 mg (60% theoretical).

Silica gel chromatography with a solvent formed by chloroform/methanol/CaCl$_2$ 0.3% (50:42:11), shows the compound to be unitary with Rf=0.35 (GM$_1$=0.43; Lyso GM$_1$=0.24) and with a fluorometric reading of 254 nm.

EXAMPLE 15

N-(4-pyridylthioacetyl)-N-lyso GM$_1$ 500 mg (0.38 mM) of Lyso GM$_1$ (prepared according to Example 2) are dissolved in 2.5 ml of dimethylformamide after which are added at room temperature 528 µl (7.6 mM) of triethylamine, 320 mg (1.9 mM) of 4-pyridylthioacetic acid and 194.2 mg (0.76 mM) of 1-methyl-2-chloropyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water (60:35:8).

The pure fractions are pooled, evaporated, treated with Na$_2$CO$_3$ 1N, dialyzed against distilled water and then concentrated to 5 ml and precipitated in 50 ml of acetone.

Product obtained: 390 mg (70% theoretical).

Silica gel chromatography with a solvent formed by chloroform/methanol/CaCl$_2$ 0.3% (50:42:11), shows the compound to be unitary with Rf=0.34 (GM$_1$=0.43; Lyso GM$_1$=0.24) and with a fluorometric reading of 254 nm.

EXAMPLE 16

N-(3-quinolincarbonyl)-N-lyso GM$_1$ 500 mg (0.38 mM) of Lyso GM$_1$ (prepared according to Example 2) are dissolved in 2.5 ml of dimethylformamide after which are added at room temperature 528 μl (7.6 mM) of triethylamine, 330 mg (1.9 mM) of 3-quinolincarboxy acid and 194.2 mg (0.76 mM) of 1-methyl-2-chloropyridinium iodide dissolved in 2.5 ml of dimethylformamide.

The mixture is left to react for 18 hrs at room temperature and then precipitated in 100 ml of acetone, filtered and dried. The product is then purified by silica gel chromatography using as eluent a mixture of chloroform/methanol/water (60:35:8).

The pure fractions are pooled, evaporated, treated with $Na_2CO_3$ 1N, dialyzed against distilled water and then concentrated to 5 ml and precipitated in 50 ml of acetone.

Product obtained: 358 mg (64% theoretical).

Silica gel chromatography with a solvent formed by chloroform methanol/$CaCl_2$ 0.3% (50:42:11), shows the compound to be unitary with Rf=0.35 ($GM_1$=0.43; Lyso $GM_1$=0.24) and with a fluorometric reading of 254 nm.

EXAMPLE 17

N-(7-theopbyllinacetyl)-N-lyso $GM_1$ 500 mg (0.38 mM) of Lyso $GM_1$ (prepared according to Example 2) are dissolved in 2.5 ml of dimethylformamide after which are added at room temperature 528 μl (7.6 mM) of triethylamine, 460 mg (1.9 mM) of 7-theophyllineacetic acid and 194.2 mg (0.76 mM) of 1-methyl-2-chloropyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water (60:35:8).

The pure fractions are pooled, evaporated, treated with $Na_2CO_3$ 1N, dialyzed against distilled water and then concentrated to 5 ml and precipitated in 50 ml of acetone.

Product obtained: 397 mg (68% theoretical).

Silica gel chromatography with a solvent formed by chloroform/methanol/$CaCl_2$ 0.3% (50:42:11), shows the compound to be unitary with Rf=0.35 ($GM_1$=0.43; Lyso $GM_1$=0.24) and with a fluorometric reading of 254 nm.

EXAMPLE 18

N-2,6-dimethoxybenzoyl-di-lyso $GM_1$ 500 mg of di-lyso $GM_1$ (0.39 mM) (prepared according to Example 1) are dissolved in 5 ml of dimethylformamide, and to this solution are then slowly added 145 mg (0.43 mM) of 9-fluorenylmethyl-oxycarbonyl-N-hydroxysuccinimide (FMOC-succ.). It is left to react for 1 hr at room temperature.

At the end of the reaction, it is precipitated in 100 ml of acetone, filtered and dried. The product is then purified by silica gel chromatography using as elution solvent a mixture of chloroform/methanol/water 60:30:6.

The fractions containing the intermediate reaction product N-FMOC-di-lyso-$GM_1$ are pooled, dried and then redissolved in 2.5 ml of dimethylformamide methanol 1:1 after which are added, at 0° C., 1.1 ml (7.92 mM) of triethylamine and 0.40 ml (3.96 mM) of methyl trifluoroacetate. It is left to react at room temperature for 3 days.

To the resulting reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 2.5 ml of dimethylformamide/methanol 1:1 and to this is added dimethoxybenzoic anhydride, freshly prepared by reacting 1.88 g (7.6 mM) of 2,6-di-methoxybenzoic acid and 5.40 mg (1.9 mM) of fluoromethylpyridinium para-toluenesulfonate in 5 ml of dimethylformamide/tetrahydrofuran 1:1. This mixture is left to react for 18 hrs at room temperature, precipitated in 100 ml of acetone, gathered with 5 ml of water and brought to pH 9.0 with NaOH 0.01N.

It is left to react at room temperature for 2 hrs to remove the trifluoroacetyl group. It is dialyzed, concentrated to 3 ml and precipitated in 15 ml of acetone.

The raw product obtained is purified by silica gel chromatography using as eluent a mixture of chloroform/methanol/water 60:35:8.

The pure fractions are pooled, evaporated, redissolved in 2 ml of chloroform/methanol 1:1 and precipitated in 10 ml of acetone.

Product obtained=283 mg (51% theoretical)

Silica gel chromatography with a solvent formed by chloroform/methanol/$CaCl_2$ 0.3% 50:42:11, shows the compound to be unitary with Rf=0.18. It proves positive to ninhydrin staining and shows a fluorometric reading of 254 nm.

EXAMPLE 19

N-2-pyridylacetyl-di-lyso $GM_1$ 500 mg of di-lyso $GM_1$ (0.39 mM) (prepared according to Example 1) are dissolved in 5 ml of dimethylformamide, and to this are then slowly added 145 mg (0.43 mM) of 9-fluorenylmethyl-oxycarbonyl-N-hydroxysuccinimide (FMOC-succ.). The mixture is left to react for 1 hr at room temperature.

At the end of the reaction, it is precipitated in 100 ml of acetone, filtered and dried. The product is then purified by silica gel chromatography using as elution solvent a mixture of chloroform/methanol/water 60:30:6.

The fractions containing the intermediate reaction product N-FMOC-di-lyso-$GM_1$ are pooled, dried and then redissolved in 2.5 ml of dimethylformamide/methanol 1:1 after which are added, at 0° C., 1.1 ml (7.92 mM) of triethylamine and 0.40 ml (3.96 mM) of methyl trifluoroacetate and it is reacted at room temperature for 3 days.

To this is then added 1 ml of piperidine to remove the fluorenyl group. It is left to react for 18 hrs at room temperature and precipitated in 100 ml of acetone/water 9:1, filtered and dried.

The intermediate reaction product is dissolved in 2.5 ml of dimethylformamide/methanol 1:1 after which are added, at room temperature, 1056 μl (7.6 mM) of triethylamine, 330 mg (1.9 mM) of 2-pyridylacetic acid hydrochloride and 194.2 mg (0.76 mM) of chloromethylpyridinium iodide dissolved in 2.5 ml of dimethylformamide.

This is left to react for 18 hrs at room temperature, precipitated in 50 ml of acetone, dissolved with 5 ml of water and brought to pH 9.0 with NaOH 0.01N. This solution is left to react at room temperature for 2 hrs to remove the trifluoroacetyl group. It is dialyzed, concentrated to 3 ml and precipitated in 15 ml of acetone.

The raw product obtained is purified by silica gel chromatography using as eluent a mixture of chloroform/methanol/water 60:35:8.

The pure fractions are pooled, evaporated, redissolved in 2 ml of chloroform/methanol 1:1 and precipitated in 10 ml of acetone.

Product obtained=296 mg (55% theoretical) Silica gel chromatography with a solvent formed by chloroform/methanol/CaCl$_2$ 0.3% 50:42:11, shows the compound to be unitary with Rf=0.19. It is positive to ninhydrin staining and shows a fluorometric reading of 254 nm.

EXAMPLE 20

N,N'-di-cycloheptanecarbonyl-di-lyso GM$_1$ 500 mg (0.39 mM) of di-lyso GM$_1$ (prepared according to Example 1) are dissolved in 2.5 ml of dimethylformamide, after which are added at room temperature 0.33 ml (2.37 mM) of triethylamine, 162 μl (1.18 mM) of cycloheptanecarboxy acid and 0.2 g (0.79 mM) of chloromethylpyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water 60:25:4.

The pure fractions are pooled, evaporated, treated with Na$_2$CO$_3$ 1N, dialyzed against distilled water and then concentrated to 5 ml and precipitated in 50 ml of acetone.

Product obtained: 407 mg (68% theoretical).

Silica gel chromatography with a solvent formed by chloroform/methanol/CaCl$_2$ 0.3% 60:35:8 shows the compound to be unitary with Rf=0.32.

EXAMPLE 21

N-N'-di-cyclopentanecarbonyl-di-lyso GM$_1$ 500 mg (0.39 mM) of di-lyso GM$_1$ (prepared according to Example 1) are dissolved in 2.5 ml of dimethylformamide after which are added at room temperature 0.33 ml (2.37 mM) of triethylamine, 123 μl (1.18 mM) of cyclopentanecarboxy acid and 0.2 g (0.79 mM) of chloromethylpyridinium iodide dissolved in 2.5 ml of dimethylformamide.

The mixture is left to react for 18 hrs at room temperature and then precipitated in 100 ml of acetone. It is filtered and dried. The product is then purified by silica gel chromatography using as eluent a mixture of chloroform/methanol/water 60:25:4.

The pure fractions are pooled, evaporated, treated with Nahd 2CO$_3$ 1N, dialyzed against distilled water and then concentrated to 5 ml and precipitated in 50 ml of acetone.

Product obtained: 277 mg (48% theoretical).

Silica gel chromatography with a solvent formed by chloroform/methanol/CaCl$_2$ 0.3% 60:35:8 shows the compound to be unitary with Rf=0.30.

EXAMPLE 22

N,N'-di-phenylacetyl-di-lyso GM$_1$ 500 mg (0.39 mM) of di-lyso GM$_1$ (prepared according to Example 1) are dissolved in 2.5 ml of dimethylformamide after which are added at room temperature 0.88 ml (6.34 mM) of triethylamine, 430 mg (3.17 mM) of phenylacetic acid and 0.2 g (0.79 mM) of chloromethylpyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water 60:25:4.

The pure fractions are pooled, evaporated, treated with Na$_2$CO$_3$ 1N, dialyzed against distilled water and then concentrated to 5 ml and precipitated in 50 ml of acetone.

Product obtained: 564 mg (95% theoretical).

Silica gel chromatography with a solvent formed by chloroform/methanol/CaCl$_2$ 0.3% 60:35:8 shows the compound to be unitary with Rf=0.32. It shows a fluorometric reading of 254 nm.

EXAMPLE 23

N,N'-di-(5-methoxy-1-indanone-3-acetyl)-di-lyso GM$_1$ 500 mg (0.39 mM) of di-lyso GM$_1$ (prepared according to Example 1) are dissolved in 2.5 ml of dimethylformamide after which are added at room temperature 0.88 ml (6.34 mM) of triethylamine, 700 mg (3.17 mM) of 5-methoxy-1-indanone-3-acetic acid and 0.2 g (0.79 mM) of chloromethylpyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water 60:25:4.

The pure fractions are pooled, evaporated, gathered with Na$_2$CO$_3$ 1N, dialyzed against distilled water and then concentrated to 5 ml and precipitated in 50 ml of acetone.

Product obtained: 601 mg (91% theoretical).

Silica gel chromatography with a solvent formed by chloroform/methanol/CaCl$_2$ 0.3% 60:35:8 shows the compound to be unitary with Rf=0.33, displaying a fluorometric reading of 254 nm.

EXAMPLE 24

N,N'-di-(2-pyridylacetyl)-di-lyso GM$_1$ 500 mg (0.39 mM) of di-lyso GM$_1$ (prepared according to Example 1) are dissolved in 2.5 ml of dimethylformamide after which are added at room temperature 0.88 ml (6.34 mM) of triethylamine, 550 mg (3.17 mM) of 2-pyridylacetic acid and 0.2 g (0.79 mM) of chloromethylpyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water 60:25:4.

The pure fractions are pooled, evaporated, treated with Na$_2$CO$_3$ 1N, dialyzed against distilled water and then concentrated to 5 ml and precipitated in 50 ml of acetone.

Product obtained: 268 mg (43% theoretical).

Silica gel chromatography with a solvent formed by chloroform/methanol/CaCl$_2$ 0.3% 60:35:8 shows the compound to be unitary with Rf=0.23. It shows a fluorometric reading of 254 nm.

EXAMPLE 25

N,N'-di-(5-methyl-2-thiophenecarbonyl)-di-lyso GM$_1$ 500 mg (0.39 mM) of di-lyso GM$_1$ (prepared according to Example 1) are dissolved in 2.5 ml of dimethylformamide after which are added at room temperature 0.88 ml (6.34 mM) of triethylamine, 450 mg (3.17 mM) of 5-methyl-2-thiophene carboxy acid and 0.2 g (0.79 mM) of chloromethylpyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water 60:25:4.

The pure fractions are pooled, evaporated, treated with $Na_2CO_3$ 1N, dialyzed against distilled water and then concentrated to 5 ml and precipitated in 50 ml of acetone.

Product obtained: 509 mg (85% theoretical).

Silica gel chromatography with a solvent formed by chloroform/methanol/$CaCl_2$ 0.3% 60:35:8 shows the compound to be unitary with Rf=0.33. It shows a fluorometric reading of 254 nm.

EXAMPLE 26

N-acetyl-N'-2-pyridylacetyl-di-lyso $GM_1$ 500 mg of di-lyso $GM_1$ (prepared according to Example 1) are dissolved in 5 ml of dimethylformamide, and to this solution are then slowly added 145 mg (0.43 mM) of 9-fluorenylmethyloxycarbonyl-N- -hydroxysuccinimide (FMOC-succ) and it is left to react for 1 hr at room temperature.

At the end of the reaction, it is precipitated in 100 ml. of acetone, filtered and dried. The product is then purified by silica gel chromatography using as elution solvent a mixture of chloroform/methanol/water 60:30:6.

The fractions containing the intermediate reaction product (N-FMOC-di-lyso-$GM_1$) are pooled, dried and then redissolved in 2.5 ml of dimethylformamide/methanol 1:1 after which are added, at room temperature, 1056 μl (7.6 mM) of triethylamine, 330 mg (1.9 mM) of 2-pyridylacetic acid hydrochloride and 194.2 mg (0.76 mM) of chloromethylpyridinium iodide dissolved in 2.5 ml of dimethylformamide. The mixture is reacted for 18 hrs at room temperature.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 30 ml of chloroform/methanol/water 1:1:0.1 after which are added 1.1 ml (7.92 ml) of triethylamine and 373 μl (3.96 mM) of acetic anhydride. It is left to react for 2 hrs at room temperature, dried, treated with 5 ml of $Na_2CO_3$ 1M and kept at 60° C. for 1 hr. It is dialyzed, concentrated to 5 ml and precipitated in 5 volumes of acetone.

The raw reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained=299 mg (54% theoretical)

Silica gel chromatography with a solvent formed by chloroform/methanol/$CaCl_2$ 0.3% 50:42:11, shows the compound to be unitary with Rf=0.37. It shows a fluorometric reading of 254 nm.

EXAMPLE 27

N-acetyl-N'-3,4,5-trimethoxybenzoyl-di-lyso $GM_1$ 500 mg of di-lyso $GM_1$ (0.39 mM) (prepared according to Example 1) are dissolved in 5 ml of dimethylformamide, and to this solution are then slowly added 145 mg (0.43 mM) of 9-fluorenylmethyloxy-carbonyl-N-hydroxysuccinimide (FMOC-succ). It is left to react for 1 hr at room temperature. At the end of the reaction, it is precipitated in 100 ml of acetone, filtered and dried. The product is then purified by silica gel chromatography using as elution solvent a mixture of chloroform/methanol/water 60:30:6. The fractions containing the intermediate reaction product (N-FMOC-di-lyso-$GM_1$) are pooled, dried and then redissolved in 2.5 ml of dimethylformamide/methanol 1:1 and to this solution is added trimethoxybenzoic anhydride dissolved in 20 ml of tetrahydrofuran, freshly prepared by reacting 0.3 g (1.9 mM) of dicyclohexylcarbodiimide and 0.3 g (1.4 mM) of trimethoxybenzoic acid in 20 ml of tetrahydrofuran and filtering away 2 hrs later the dicyclohexylurea which has formed.

The condensation reaction is conducted at 25° C. for 18 hrs under stirring.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 30 ml of chloroform/methanol/water 1:1:0.1 after which are added 1.1 ml (7.92 ml) of triethylamine and 373 μl (3.96 mM) of acetic anhydride. It is left to react for 2 hrs at room temperature, dried, treated with 5 ml of $Na_2CO_3$ 1M and kept at 60° C. for 1 hr. It is dialyzed, concentrated to 5 ml and precipitated in 5 volumes of acetone.

The raw reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained=286 mg (49% theoretical)

Silica gel chromatography with a solvent formed by chloroform/methanol/$CaCl_2$ 0.3% 50:42:11, shows the compound to be unitary with Rf=0.39. It shows a fluorometric reading of 254 nm.

EXAMPLE 28

N-dichloroacetyl-N'-2-pyridylacetyl-di-lyso $GM_1$ 500 mg of di-lyso $GM_1$ (0.39 mM) (prepared according to Example 1) are dissolved in 5 ml of dimethylformamide, and to this solution are then slowly added 145 mg (0.43 mM) of 9-fluorenylmethyloxy- carbonyl-N-hydroxysuccinimide (FMOC-succ). It is left to react for 1 hr at room temperature.

At the end of the reaction, it is precipitated in 100 ml of acetone, filtered and dried. The product is then purified by silica gel chromatography using as elution solvent a mixture of chloroform/methanol/water 60:30:6. The fractions containing the intermediate reaction product (N-FMOC-di-lyso-$GM_1$) are pooled, dried and then redissolved in 2.5 ml of dimethylformamide/methanol 1:1 after which are added, at room temperature, 1056 μl (7.6 mM) of triethylamine, 330 mg (1.9 mM) of 2-pyridylacetic acid hydrochloride and 194.2 g (0.76 mM) of chloromethylpyridinium iodide dissolved in 2.5 ml of dimethylformamide. It is reacted at room temperature for 18 hr.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 30 ml of chloroform/methanol/water 1:1:0.1 after which are added 1.1 ml (7.92 ml) of triethylamine and 950 mg (3.96 mM) of dichloroacetic anhydride. It is left to react for 2 hrs at room temperature, dried, treated with 5 ml of $Na_2CO_3$ 1M and kept at 60° C. for 1 hr. It is dialyzed, concentrated to 5 ml and precipitated in 5 volumes of acetone.

The reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained=267 mg (46% theoretical)

Silica gel chromatography with a solvent formed by chloroform/methanol/$CaCl_2$ 0.3% 50:42:11, shows the compound to be unitary with Rf=0.40. It shows a fluorometric reading of 254 nm.

EXAMPLE 29

N-dichloroacetyl-N'-3,4,5-trimethoxybenzoyl-di-lyso $GM_1$ 500 mg of di-lyso GM (0.39 mM) (prepared according to Example 1) are dissolved in 5 ml of dimethylformamide, and to this solution are then slowly added 145 mg (0.43 mM) of 9-fluorenylmethyloxy- carbonyl-N-hydroxysuccinimide (FMOC-succ) and it is left to react for 1 hr at room temperature.

At the end of the reaction, the resulting mixture is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso-$GM_1$) are pooled, dried and then redissolved in 2.5 ml of dimethylformamide/methanol 1:1 and to this is added trimethoxybenzoic anhydride dissolved in 10 ml of tetrahydrofuran, freshly prepared by reacting 0.3 g (1.9 mM) of dicyclohexylcarbodiimide and 0.3 g (1.4 mM) of trimethoxybenzoic acid in 10 ml of tetrahydrofuran and filtering away 2 hrs later the dicyclohexylurea which has formed.

The condensation reaction is conducted at 25° C. for 18 hrs under stirring.

To this is then added 1 ml of piperidine to remove the fluorenyl group, and the mixture is left to react for 18 hrs at room temperature and precipitated in 100 ml of acetone/water 9:1, filtered and dried. The intermediate reaction product is dissolved in 30 ml of chloroform/methanol/water 1:1:0.1 after which are added 1.1 ml (7.92 ml) of triethylamine and 950 mg (3.96 mM) of dichloroacetic anhydride. It is left to react for 2 hrs at room temperature, dried, treated with 5 ml of $Na_2CO_3$ 1M and kept at 60° C. for 1 hr. It is dialyzed, concentrated to 5 ml and precipitated in 5 volumes of acetone.

The raw reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained=293 mg (48% theoretical)

Silica gel chromatography with a solvent formed by chloroform/methanol/$CaCl_2$ 0.3% 50:42:11, shows the compound to be unitary with Rf=0.41 and having a fluorometric reading of 254 nm.

EXAMPLE 30

N-2-furoyl-N'-butyryl-di-lyso $GM_1$ 500 mg of di-lyso $GM_1$ (0.39 mM) (prepared according to Example 1) are dissolved in 5 ml of dimethylformamide, and to this solution are then slowly added 145 mg (0.43 mM) of 9-fluorenylmethyl-oxycarbonyl-N-hydroxysuccinimide (FMOC-succ). It is left to react for 1 hr at room temperature.

At the end of the reaction, it is precipitated in 100 ml of acetone, filtered and dried. The product is then purified by silica gel chromatography using as elution solvent a mixture of chloroform/methanol/water 60:30:6. The fractions containing the intermediate reaction product (N-FMOC-di-lyso-$GM_1$) are pooled, dried and then redissolved in 2.5 ml of dimethylformamide/methanol 1:1 after which are added, at 0° C., 1.1 ml (7.92 mM) of triethylamine and 626 mg (3.96 mM) of butyric anhydride. It is left to react at room temperature for 2 hrs.

To this reaction mixture is then added 1 ml of piperidine to remove the fluorenyl group, and it is left to react for 18 hrs at room temperature and precipitated in 100 ml of acetone/water 9:1, filtered and dried.

The intermediate reaction product is dissolved in 2.5 ml of dimethylformamide after which are added at room temperature 528 μl (3.8 mM) of triethylamine, 210 mg (1.9 mM) of 2-furoic acid and 194.2 mg (0.76 Mm) of chloromethylpyridinium iodide dissolved in 2.5 ml of dimethylformamide.

It is left to react for 18 hrs at room temperature and then precipitated in 100 ml of acetone, filtered and dried. The product is then purified by silica gel chromatography using as eluent a mixture of chloroform/methanol/water 60:35:8.

The pure fractions are pooled, evaporated, redissolved in 2.0 ml of chloroform/methanol 1:1 and precipitated in 10 ml of acetone.

Product obtained=289 mg (52% theoretical)

Silica gel chromatography with a solvent formed by chloroform/methanol/$CaCl_2$ 0.3% 50:42:11, shows the compound to be unitary with Rf=0.39. It shows a fluorometric reading of 254 nm.

EXAMPLE 31

N-2,6-dimethoxybenzoyl-N'-butyryl-di-lyso $GM_1$ 500 mg of di-lyso $GM_1$ (0.39 Mm) (prepared according to Example 1) are dissolved in 5 ml of dimethylformamide, and to this solution are then slowly added 145 mg (0.43 mM) of 9-fluorenylmethyloxy- carbonyl-N-hydroxysuccinimide (FMOC-succ). It is left to react for 1 hr at room temperature.

At the end of the reaction, it is precipitated in 100 ml of acetone, filtered and dried. The product is then purified by silica gel chromatography using as elution solvent a mixture of chloroform/methanol/water 60:30:6. The fractions containing the intermediate reaction product (N-FMOC-di-lyso-$GM_1$) are pooled, dried and then redissolved in 2.5 ml of dimethylformamide/methanol 1:1 after which are added, at 0° C., 1.1 ml (7.92 mM) of triethylamine and 626 mg (3.96 mM) of butyric anhydride and it is reacted at room temperature for 2 hrs.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 1 ml of dimethylformamide after which are added at room temperature 1.056 ml (7.6 mM) of triethylamine and 2,6-dimethoxybenzoic anhydride, freshly prepared by reacting 2.76 g (15.2 mM) of 2,6-dimethoxybenzoic acid and 1.08 g (3.8 mM) of fluoromethylpyridinium para-toluenesulfonate in 10 ml of dimethylformamide/tetrahydrofuran 1:1. The condensation reaction is conducted at room temperature for 4 hrs under stirring. At the end of the reaction, the solution is concentrated to 5 ml, precipitated in 50 ml of acetone, filtered and vacuum-dried.

Silica gel chromatography is effected, using as eluent a mixture of chloroform/methanol/water 60:35:8.

The pure fractions are pooled, evaporated, treated with $Na_2CO_3$ 1N, dialyzed against distilled water and then concentrated to 5 ml and precipitated in 50 ml of acetone.

Product obtained=297 mg (51% theoretical)

Silica gel chromatography with a solvent formed by chloroform/methanol/$CaCl_2$ 0.3% 50:42:11, shows the compound to be unitary with Rf=0.37. It shows a fluorometric reading of 254 nm.

EXAMPLE 32

N-2-pyridylacetyl-N'-lauroyl-di-lyso $GM_1$ 500 mg of di-lyso $GM_1$ (0.39 mM) (prepared according to Example 1) are dissolved in 5 ml of dimethylformamide, and to this solution are then slowly added 145 mg (0.43 mM) of 9-fluorenylmethyloxy- carbonyl-N-hydroxysuccinimide (FMOC-succ). It is left to react for 1 hr at room temperature.

At the end of the reaction, it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso-$GM_1$) are pooled, dried and then redissolved in 2.5 ml of dimethylformamide/methanol 1:1 after which are added, at 0° C., 1.1 ml (7.92 mM) of triethylamine and 1.51 g (3.96 mM) of lauric anhydride and this is reacted at room temperature for 18 hrs.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 2.5 ml of dimethylformamide/methanol 1:1 after which are added at room temperature 1056 μl (7.6 ml) of triethylamine, 330 mg (1.9 mM) of 2-pyridylacetic acid hydrochloride and 194.2 mg (0.76 mM) of chloromethylpyridinium iodide dissolved in 2.5 ml of dimethylformamide. It is reacted for 18 hrs at room temperature and then precipitated in 100 ml of acetone.

The raw reaction product is purified by silica gel chromatography using as elution solvent a mixture of chloroform/methanol 60:35:8.

The pure fractions are pooled, evaporated, redissolved in 2.0 ml of chloroform/methanol 1:1 and precipitated in 10 ml of acetone.

Product obtained=262 mg (43% theoretical)

Silica gel chromatography with a solvent formed by chloroform/methanol/$CaCl_2$ 0.3% 50:42:11, shows the compound to be unitary with Rf=0.61. It displays a fluorometric reading of 254 nm.

EXAMPLE 33

N'-3,4,5-trimethoxybenzoyl-N'-lauroyl-di-lyso $GM_1$ 500 mg of lyso $GM_1$ (0.39 mM) (prepared according to Example 1) are dissolved in 5 ml of dimethylformamide, and to this are then slowly added 145 mg (0.43 mM) of 9-fluorenylmethyloxycarbonyl-N-hydroxysuccinimide (FMOC-succ). It is left to react for 1 hr at room temperature. At the end of the reaction it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso-$GM_1$) are pooled, dried and then redissolved in 2.5 ml of dimethyl formamide/methanol 1:1 after which are added, at 0° C., 1.1 ml (7.92 mM) of triethylamine and 1.51 g (3.96 mM) of lauric anhydride. It is reacted at room temperature for 18 hrs.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 2.5 ml of dimethylformamide/methanol 1:1 and to this solution is added trimethoxybenzoic anhydride dissolved in 10 ml of tetrahydrofuran, freshly prepared by reacting 0.3 g (1.9 Mm) of dicyclohexylcarbodiimide and 0.3 g (1.4 mM) of trimethoxybenzoic acid in 10 ml of tetrahydrofuran and filtering away, 2 hrs later, the dicyclohexylurea which has formed.

The condensation reaction is conducted at 25° C. for 18 hrs under stirring and then the product is precipitated in 100 ml of acetone.

The raw reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained=294 mg (46% theoretical)

Silica gel chromatography with a solvent formed by chloroform/methanol/$CaCl_2$ 0.3% 50:42:11 shows the product to be a unitary compound with Rf=0.63. Its fluorometric reading is 254 nm.

EXAMPLE 34

N-3,4,5-trimethoxybenzoyl-N'-2-pyridylacetyl-di-lyso $GM_1$ 500 mg of di-lyso $GM_1$ (0.39 mM) (prepared according to example 1) are dissolved in 5 ml of dimethylformamide.

To this solution are then slowly added 145 mg (0.43 mM) of 9-fluorenylmethyloxycarbonyl-N-hydroxysuccinimide (FMOC-succ) and it is left to react for 1 hour at room temperature.

At the end of the reaction, it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso-GM$_1$) are pooled, dried and then redissolved in 2.5 ml of dimethylformamide/methanol 1:1 and to this solution are added, at room temperature, 1056 µl (7.6 mM) of triethylamine and 330 mg (1.9 mM) of 2-pyridylacetic acid hydrochloride and 194.2 mg (0.76 mM) of chloromethylpyridinium iodide dissolved in 2.5 ml of dimethylformamide. It is left to react at room temperature for 18 hrs.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 2.5 ml of dimethylformamide/methanol 1:1 and to this solution is added trimethoxybenzoic anhydride dissolved in 10 ml of tetrahydrofuran, freshly prepared by reacting 0.3 g (1.9 mM) of dicyclohexylcarbodiimide and 0.3 g (1.4 mM) of trimethoxybenzoic acid in 10 ml of tetrahydrofuran and filtering away, 2 hrs later, the dicyclohexylurea which has formed.

The condensation reaction is conducted at 25° C. for 18 hrs under stirring and then the product is precipitated in 100 ml of acetone.

The raw reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained = 243 mg (43% theoretical)

Silica gel chromatography with a solvent formed by chloroform/methanol/CaCl$_2$ 0.3% 50:42:11 shows the product to be a unitary compound with Rf=0.59. Its fluorometric reading is 254 nm.

EXAMPLE 35

N-2-pyridylacetyl-N'-2,6-dimethoxybenzoyl-di-lyso GM$_1$ 500 mg of di-lyso GM$_1$ (0.39 mM) (prepared according to Example 1) are dissolved in 5 ml of dimethylformamide, and to this solution are then slowly added 145 mg (0.43 mM) of 9-fluorenylmethyloxycarbonyl-N-hydroxysuccinimide (FMOC-succ). It is left to react for 1 hour at room temperature.

At the end of the reaction, it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso-GM$_1$) are pooled, dried and then redissolved in 2.5 ml of dimethylformamide/methanol 1:1 and to this solution is added dimethoxybenzoic anhydride, freshly prepared by reacting 1.88 g (1.6 mM) of 2,6-dimethoxybenzoic acid and 540 mg (1.9 mM) of fluoromethylpyridinium para-toluenesulfonate in 5 ml of dimethylformamide/tetrahydrofuran 1:1, which is then left to react at room temperature for 4 hrs.

1 ml of piperidine is then added to remove the fluorenyl groups. The mixture is left to react for 18 hrs at room temperature and then precipitated in 100 ml of acetone/water 9:1, filtered and dried.

The intermediate reaction product is dissolved in 2.5 ml of dimethylformamide/methanol 1:1 and to this are added, at room temperature, 1056 µl (7.6 mM) of triethylamine, 330 mg (1.9 mM) of 2-pyridylacetic acid hydrochloride and 194.2 mg (0.76 mM) of chloromethylpyridinium iodide dissolved in 2.5 ml of dimethylformamide. It is reacted at room temperature for 18 hrs and then the product is precipitated in 100 ml of acetone.

The raw reaction product is purified by silica gel chromatography using as elution solvent a mixture of chloroform/methanol/water 60:35:8.

The pure fractions are pooled, evaporated, redissolved in 2.0 ml of chloroform/methanol 1:1 and precipitated in 10 ml of acetone.

Product obtained = 247 mg (41% theoretical)

Silica gel chromatography with a solvent formed by chloroform/methanol/CaCl$_2$ 0.3% 50:42:11 shows the product to be a unitary compound with Rf=0.58 with a fluorometric reading of 254 nm.

EXAMPLE 36

N'-3,4,5-trimethoxybenzoyl-N'-lyso GM$_1$ 500 mg (0.33 mM) of N'-lyso GM$_1$ are dissolved in 50 ml of chloroform/methanol 1:1 and to this solution is added 0.28 g (0.7 mM) of trimethoxybenzoic anhydride dissolved in 20 ml of tetrahydrofuran, and freshly prepared by reacting 0.3 g (1.9 mM) of dicyclohexylcarbodiimide and 0.3 g (1.4 mM) of trimethoxybenzoic acid in 20 ml of tetrahydrofuran, and filtering away, 2 hrs later, the dicyclohexylurea which has formed.

The condensation reaction is conducted at 25° C. for 18 hrs under stirring.

At the end of the reaction, the product is dried, gathered with 5 ml of chloroform/methanol 1:1 and precipitated in 100 ml of acetone.

The raw product thus obtained is purified by silica gel chromatography using as elution solvent a mixture of chloroform/methanol/water 60:15:2.

The pure fractions are pooled, evaporated, redissolved in 5 ml of chloroform/methanol 1:1 and the product is precipitated with 100 ml of acetone.

Product obtained: 320 mg (56.7% theoretical).

Silica gel chromatography with a solvent formed by chloroform/methanol/CaCl$_2$ 2 0.3% 60:35:8 shows the product to be a fluorescent unitary compound with an Rf of 0.50.

EXAMPLE 37

N'-2-furoyl-di-lyso GM$_1$ 500 mg of di-lyso GM$_1$ (0.39 mM) (prepared according to Example 1) are dissolved in 5 ml of dimethylformamide, and to this solution are then slowly added 145 mg (0.43 mM) of 9-fluorenylmethyloxycarbonyl-N-hydroxysuccinimide dissolved in 2 ml of tetrahydrofuran. It is left to react for 1 hour at room temperature.

At the end of the reaction, 528 µl (3.8 mM) of triethylamine, 210 mg (1.9 mM) of 2-furoic acid and 194.2 mg (0.76 mM) of chloromethylpyridinium iodide dissolved in 2.5 ml of dimethylformamide are added at room temperature. This mixture is then left to react for 18 hrs at room temperature after which are added 2 ml of piperidine to remove the protector group.

This is left to react for 18 hrs at room temperature and then precipitated in 100 ml of acetone, filtered and dried. The product thus obtained is dissolved in 10 ml Na$_2$CO$_3$ 1M and kept at 60° C. for 1 hour. It is dialyzed, concentrated to 5 ml and precipitated in 5 volumes of acetone.

The raw reaction product is purified by silica gel chromatography using as elution solvent a mixture of chloroform/methanol/NH$_3$ 2.5N 60:35:8.

The fractions containing the pure product are dried and then redissolved in 5 ml of water. The solution is brought to pH 10 with NaOH 0.01N and dialyzed, concentrated to 5 ml and precipitated in 50 ml of acetone.

Product obtained: 301 mg (57% theoretical).

Silica gel chromatography with a solvent formed by chloroform/methanol/CaCl$_2$ 0.3% 50:42:11 shows the product to be unitary with Rf=0.31, positive to ninhydrin staining. Its fluorometric reading is 254 nm.

EXAMPLE 38

N'-4,5-trimethoxybenzoyl-di-lyso GM$_1$ 500 mg of di-lyso GM$_1$ (0.39 mM) (prepared according to Example 1) are dissolved in 5 ml of dimethylformamide, and to this solution are then slowly added 145 mg (0.43 mM) of 9-fluorenylmethyloxycarbonyl-N-hydroxysuccinimide dissolved in 2 ml of tetrahydrofuran, and it is left to react for 1 hour at room temperature.

At the end of the reaction, trimethoxybenzoic anhydride is added, dissolved in 20 ml of tetrahydrofuran, freshly prepared by reacting 0.3 g (1.9 mM) of dicyclohexylcarbodiimide and 0.3 g (1.4 mM) of trimethoxybenzoic acid in 20 ml of tetrahydrofuran, and filtering away, 2 hrs later, the dicyclohexylurea which has formed.

The condensation reaction is conducted at 25° C. for 18 hrs under stirring. 2 ml of piperidine are then added to remove the protector group, and it is left to react for 18 hrs at room temperature and then precipitated in 100 ml of acetone. It is filtered and dried. The product thus obtained is dissolved in 10 ml Na$_2$CO$_3$ 1M and kept at 60° C. for 1 hour. It is dialyzed, concentrated to 5 ml and precipitated in 5 volumes of acetone. The raw reaction product is purified by silica gel chromatography using as elution solvent a mixture of chloroform/methanol/NH$_3$ 2.5N 60:35:8. The fractions containing the pure product are dried and then redissolved in 5 ml of water. It is brought to pH 10 with NaOH 0.01N and dialyzed, concentrated to 5 ml and precipitated in 50 ml of acetone.

Product obtained: 317.5 mg (56% theoretical).

Silica gel chromatography with a solvent formed by chloroform/methanol/CaCl$_2$ 0.3% 50:42:11 shows the product to be unitary with Rf=0.35, positive to ninhydrin staining. Its fluorometric reading is 254 nm.

EXAMPLE 39

Preparation of a Ganglioside Mixture (GA Mixture) by Extraction from Bovine Brain Tissue Bovine brain cortex is removed from the animal and homogenized in phosphate buffer to pH 6.8; to this are then added 6 volumes of tetrahydrofuran and the resulting mixture is centrifuged. The supernatant is then reextracted twice with tetrahydrofuran. After centrifugation the non-polar materials are removed by partitioning with ethyl ether and the aqueous-tetrahydrofuran phase is introduced into the ion exchange column equilibrated with 50% ethanol. To the product from the column is added barium hydroxide and four volumes of iced ethanol. After 18 hrs cooling, a precipitate is gathered which is then slightly acidified with hydrochloric acid, after dissolution in water. The solution thus obtained is dialyzed and freeze-dried. The yield at this point is approx. 0.6 mg of raw ganglioside mixture per gram of nervous tissue. The freeze-dried powder is dispersed in 20 volumes of chloroform-methanol 2:1, and once the solution obtained has been filtered to perfect clearness, it is then partitioned by adding 0.2 volumes of a solution of potassium chloride in water at 0.88%.

The upper layer is separated, dialyzed and freeze-dried. The final yield is approximately 0.3 mg of purified mixture of ganglioside salts per gram of brain tissue. The ganglioside mixture obtained can be fractioned in various portions representing substantially pure gangliosides (in the sense as already described above), using columns of silicic acid and eluting with mixtures of methanol-chloroform. Thus, an average composition of approximately 40% of ganglioside GD$_{1a}$, 21% of ganglioside GM$_1$, 19% of ganglioside GT$_{1b}$ and 16% of ganglioside GD$_{1b}$ is obtained.

EXAMPLE 40

2-furoyl derivatives of a mixture of N-lysogangliosides

1) Preparation of N-lysogangliosides 10 g of the ganglioside mixture (obtained according to Example 39 are dissolved in 200 ml of KOH 3N and hydrolysis is conducted for 72 hrs at 90° C. The solution is then cooled and brought to pH 6.5 with hydrochloric acid. It is left to stand for 18 hrs at 4° C. and then the precipitated fatty acids are filtered away. It is dialyzed against water and concentrated to 500 ml and precipitated in 5 lt of acetone.

The product containing the N'-lysogangliosides and N,N'-di-lysogangliosides (<20%) is vacuum-dried and then redissolved in 100 ml of dimethylformamide.

To this solution are then slowly added 2.15 g (6.37 mM) of 9-fluorenylmethyloxycarbonyl-N-hydroxysuccinimide dissolved in 20 ml of tetrahydrofuran and it is left to react for 1 hour at room temperature. Finally, 3 ml (31.85 mM) of acetic anhydride and 0.9 ml (63.7 mM) of triethylamine are added. After 30 minutes, 12.5 ml of piperidine are added to remove the protecting group. It is left to react for 18 hrs at room temperature and precipitated in 2 lt of acetone and dried. The material thus obtained is dissolved in Na$_2$CO$_3$ 1M and kept at 60° for 1 hour. It is dialyzed, concentrated to 100 mg/ml and precipitated in 5 volumes of acetone. The product is passed through an S-Sepharose column (H$^+$ form) equilibrated in methanol. It is washed with methanol, thus obtaining the N-lysogangliosides by eluting with NH$_4$Cl 10 mM in methanol.

The fractions containing the product are dried and then redissolved in water. They are brought to pH 10 with NaOH 0.01N and dialyzed, concentrated to 100 mg/ml and precipitated in 5 volumes of acetone.

Product obtained: 4.7 g (55% theoretical).

2) Preparation of the 2-furoyl Derivative 500 mg (0.31 mM) of the previously prepared mixture of N-lysogangliosides are dissolved in 2.5 ml of dimethylformamide and to this solution are added 431 μl (3.1 mM) of triethylamine, 174 mg (1.55 mM) of 2-furoic acid and 158.4 mg (0.62 mM) of 1-methyl-2-chloropyridinium iodide dissolved in 2.5 ml of dimethylformamide.

It is reacted for 18 hrs at room temperature and then the product is precipitated in 10 ml of acetone. It is filtered and dried.

The acylated product is separated from the compound which has not reacted by chromatography on an S-Sepharose column (H+ form) equilibrated in methanol. The furoyl derivative is eluted in methanol, dried, gathered with $Na_2CO_3$ 1N, dialyzed, concentrated to 2.5 ml and precipitated in 25 ml of acetone.

Product obtained: 373 mg (72% theoretical).

EXAMPLE 41

Methyl ester of N-(2-furoyl)-N-lyso $GM_1$ 500 mg (0.36 mM) of the N-(2-furoyl)-N-lyso $GM_1$ sodium salt (prepared according to Example 7) are dissolved in 5 ml of N-methylpyrrolidone and to this solution are added 44.5 μl (0.72 mM) of methyl iodide. It is left to react for 3 hrs at room temperature, precipitated in ethyl acetate, filtered and vacuum-dried.

The product is then purified by silica gel chromatography using as eluent a mixture of chloroform/methanol/water (60:30:6).

The pure fractions are pooled, evaporated, redissolved in 2.5 ml of chloroform/methanol 1:1 and precipitated in 25 ml of acetone.

Product obtained: 449 mg (89% theoretical).

Silica gel chromatography with a solvent formed by chloroform/methanol/$CaCl_2$ 0.3% (50:42:11), shows the compound to be unitary with Rf=0.4 [N-(2-furoyl) lyso $GM_1$=0.37].

EXAMPLE 42

Peracetylate of the methyl ester of N-(2-furoyl)-N-lyso $GM_1$ 500 mg (0.36 mM) of the methyl ester of N-(2-furoyl)-N-lyso $GM_1$ (prepared according to Example 41) are dissolved in 5 ml of pyridine and to this solution are added 2.5 ml of acetic anhydride, freshly distilled, and the mixture is stirred for 72 hrs at room temperature. At the end of the reaction, the solution is evaporated in a rotary evaporator and the residue is partitioned between 10 ml of iced water and 10 ml of ethyl acetate; the ethyl acetate is washed in cold HCl 1M, with water and with a solution of $NaHCO_3$ 1M. The organic phases are anhydrified with sodium sulfate, evaporated and the residue is purified by silica gel chromatography, using a mixture of dichloromethane/ethyl acetate/isopropanol (70:30:45). The pure fractions are pooled, evaporated, redissolved in 5 ml of ethyl ether and precipitated in 25 ml of n-hexane.

Product obtained: 463 mg (62% theoretical).

Silica gel chromatography with a solvent formed by chloroform/methanol/ethyl acetate (70:10:30) and ethyl acetate/isopropanol (95:5), shows the product to be unitary with Rf of 0.45 and 0.26, respectively.

EXAMPLE 43

Inner ester of N-(2-furoyl)-N-lyso $GM_1$ 500 mg (0.36 mM) of N-(2-furoyl)-N-lyso $GM_1$ sodium salt are dissolved in 5 ml of N-methylpyrrolidone at 4° C. and reacted with 55 μl (0.4 mM) of triethylamine and 100 mg (0.41 mM) of 1-methyl-2-chloropyridinium iodide. The reaction is conducted for 4 hrs with a quantitative yield. The product is precipitated by adding 50 ml of acetone, and it is filtered, gathered with 5 ml of chloroform/isopropanol 1:1 and reprecipitated in 25 ml of acetone.

Product obtained: 476 mg (96% theoretical).

Silica gel chromatography with a solvent formed by chloroform/methanol/$CaCl_2$ 0.3% (50:42:11), shows the compound to be unitary with Rf=0.44 [N-(2-furoyl)-N-lyso $GM_1$=0.37].

EXAMPLE 44

2-butylamide of N-(2-furoyl)-N-lyso $GM_1$ 500 mg (0.36 mM) of the methyl ester of N-(2-furoyl)-N-lyso $GM_1$ (prepared according to Example 41) are dissolved in 5 ml of pyridine and to this solution are added 2.5 ml of 2-butylamine. It is reacted for 72 hrs at room temperature and then dried in a rotary evaporator, dissolved with 5 ml of chloroform/methanol 1:1 and precipitated in 25 ml of acetone. It is filtered and vacuum-dried.

The product is then purified by silica gel chromatography using as eluent a mixture of chloroform/methanol/water (60:25:4).

The pure fractions are pooled, evaporated, redissolved in 2.5 ml of chloroform/methanol 1:1 and precipitated in 25 ml of acetone.

Product obtained: 376 mg (75% theoretical).

Silica gel chromatography with a solvent formed by chloroform/methanol/$CaCl_2$ 0.3% (50:42:11), shows the compound to be unitary with Rf=0.50 [methyl ester of N-(2-furoyl)-N-lyso $GM_1$=0.42].

Pharmaceutical Preparations in Injectable Solutions

EXAMPLE 45

| Preparation No. 1 - one 2 ml vial contains: | |
| --- | --- |
| - active substance | 5 mg |
| - sodium chloride | 16 mg |
| - citrate buffer pH 6 in water for injection to | 2 ml |

The active substance is chosen from the group formed by the ganglioside derivatives described in either one of Examples 5 and 12.

| Preparation No. 2 - one 2 ml vial contains: | |
| --- | --- |
| - active substance | 50 mg |
| - sodium chloride | 16 mg |
| - citrate buffer pH 6 in water for injection to | 2 ml |

The active substance is chosen from the group formed by the ganglioside derivatives described in Example 7.

| Preparation No. 3 - one 4 ml flacon contains: | |
| --- | --- |
| - active substance | 100 mg |
| - sodium chloride | 32 mg |
| - citrate buffer pH 6 in water for injection to | 4 ml |

The active substance is chosen from the group formed by the ganglioside derivatives described in Examples 27, 29, 38 and 40.

Pharmaceutical Compositions Prepared in Twin Flacons

EXAMPLE 46

The preparations illustrated in this Example are presented in twin flacons. The first flacon contains the active substance in the form of a freeze-dried powder in quantities varying between 10% and 90% by weight together with a pharmaceutically acceptable excipient, such as glycine or mannitol. The second flacon contains the solvent, as a sodium chloride solution, and a citrate buffer. Immediately prior to administration the contents of the two flacons are mixed together and the freeze-dried powder containing the active substance dissolves rapidly, forming an injectable solution. The pharmaceutical form comprised of a flacon containing the active substance in the form of a freeze-dried powder, is the preferred form of the present invention.

| System No. 1 | |
|---|---|
| a. one 2 ml flacon of freeze-dried substance contains: | |
| - active substance | 5 mg |
| - glycine | 30 mg |
| b. one 2 ml vial of solvent contains: | |
| - sodium chloride | 16 mg |
| - citrate buffer in water for injection to | 2 ml |

The active substance is chosen from the group formed by the ganglioside derivatives described in either one of Examples 5 and 12.

| System No. 2 | |
|---|---|
| a. one 3 ml vial of freeze-dried substance contains: | |
| - active substance | 5 mg |
| - mannitol | 40 mg |
| b. one 2 ml vial of solvent contains: | |
| - sodium chloride | 16 mg |
| - citrate buffer in water for injection to | 2 ml |

The active substance is chosen from the group formed by the ganglioside derivatives described in either one of Examples 5 and 12.

| System No. 3 | |
|---|---|
| a. one 3 ml vial of freeze-dried substance contains: | |
| - active substance | 50 mg |
| - glycine | 25 mg |
| b. one 3 ml vial of solvent contains: | |
| - sodium chloride | 24 mg |
| - citrate buffer in water for injection to | 3 ml |

The active substance is chosen from the group formed by the ganglioside derivatives described in any one of Examples 18, 33 and 38.

| System No. 4 | |
|---|---|
| a. one 3 ml vial of freeze-dried substance contains: | |
| - active substance | 50 mg |
| - mannitol | 20 mg |
| b. one 3 ml vial of sobvent contains: | |
| - sodium chloride | 24 mg |
| - citrate buffer in water for injection to | 3 ml |

The active substance is chosen from the group formed by the ganglioside derivatives described in any one of Examples 18, 33 and 38.

| System No. 5 | |
|---|---|
| a. one 5 ml flacon of freeze-dried substance contains: | |
| - active substance | 150 mg |
| - glycine | 50 mg |
| b. one 4 ml vial of solvent contains: | |
| - sodium chloride | 32 mg |
| - citrate buffer in water for injection to | 4 ml |

The active substance is chosen from the group formed by the ganglioside derivatives described in any one of Examples 27, 29, 38 and 40.

| System No. 6 | |
|---|---|
| a. one 5 ml flacon of freeze-dried substance contains: | |
| - active substance | 100 mg |
| - mannitol | 40 mg |
| b. one 4 ml vial of solvent contains: | |
| - sodium chloride | 32 mg |
| - citrate buffer in water for injection to | 4 ml |

The active substance is chosen from the group formed by the ganglioside derivatives described in any one of Examples 27, 29, 38 and 40.

| System No. 7 | |
|---|---|
| a. one 3 ml flacon contains: | |
| - sterile, micronized active substance | 40 mg |
| b. one 3 ml vial of solvent contains: | |
| - Tween 80 | 10 mg |
| - sodium chloride | 24 mg |
| - phosphate buffer in water for injection to | 3 ml |

The active substance is chosen from the group formed by the ganglioside derivatives described in any one of Examples 41, 42 and 43.

| System No. 8 | |
|---|---|
| a. one 5 ml flacon contains: | |
| - sterile, micronized active substance | 100 mg |
| b. one 4 ml vial of solvent contains: | |
| - Tween 80 | 15 mg |
| - soybean lecithin | 5 mg |
| - sodium chloride | 36 mg |
| - citrate buffer in water for injection to | 4 ml |

The active substance is chosen from the group formed by the ganglioside derivatives described in any one of Examples 41, 42 and 43.

Pharmaceutical Preparations for Transdermal Administration

EXAMPLE 47

| Preparation No. 1 - one plaster contains: | |
|---|---|
| - active substance | 100 mg |
| - glycerol | 1.6 g |
| - polyvinyl alcohol | 200 mg |
| - polyvinylpyrrolidone | 100 mg |
| - excipient to enhance transdermal penetration | 20 mg |
| - water | 1.5 g |

The active substance is chosen from the group formed by the ganglioside derivatives described in any one of Examples 22, 23 and 25.

| Preparation No. 2 - 100 g of ointment contain: | |
| --- | --- |
| - active substance (in 5 g of mixed phospholipid liposomes) | 4.0 g |
| - polyethylene glycol monostearate | 1.5 g |
| - glycerol | 1.5 g |
| - ester of p-hydroxybenzoic acid | 125 mg |
| - water | 72.9 g |

The active substance is chosen from the group formed by the ganglioside derivatives described in any one of Examples 22, 23 and 25.

Pharmaceutical Preparations for Oral Administration

EXAMPLE 48

| Preparation No. 1 - one tablet contains: | |
| --- | --- |
| - active substance | 20 mg |
| - microcrystalline cellulose | 150 mg |
| - lactose | 20 mg |
| - amide | 10 mg |
| - magnesium stearate | 5 mg |

The active substance is chosen from the group formed by the ganglioside derivatives described in any one of Examples 9, 13, 19 and 26.

| Preparation No. 2 - one pill contains: | |
| --- | --- |
| - active substance | 30 mg |
| - carboxymethyl cellulose | 150 mg |
| - amide | 15 mg |
| - shellac | 10 mg |

| Preparation No. 2 - one pill contains: | |
| --- | --- |
| - saccharose | 35 mg |
| - coloring | 0.5 mg |

The active substance is chosen from the group formed by the ganglioside derivatives described in any one of Examples 9, 14 and 28.

| Preparation No. 3 one gelatinous capsule contains: | |
| --- | --- |
| - active substance | 40 mg |
| - lactose | 100 mg |
| - gastroresistant coating | 5 mg |

The active substance is chosen from the group formed by the ganglioside derivatives described in any one of Examples 15, 24 and 24.

| Preparation No. 4 - one soft gelatin capsule contains: | |
| --- | --- |
| - active substance | 50 mg |
| - vegetable oil | 200 mg |
| - beeswax | 20 mg |
| - gelatin | 150 mg |
| - glycerol | 50 mg |
| - coloring | 3 mg |

The active substance is chosen from the group formed by the ganglioside derivatives described in any one of Examples 15, 24 and 34.

The following is claimed:

1. A pharmaceutical composition comprising a therapeutically effective amount of N-(2-thiopheneacetyl)-N'-acetyl-N,N'-di-lyso $GM_1$ as the active ingredient, together with a pharmaceutically acceptable excipient.

2. An N,N'-diacyl-N,N'-di-lysoganglioside which is N-(2-thiopheneacetyl)-N'-acetyl-N,N'-di-lyso $GM_1$.

* * * * *